United States Patent [19]

Soma et al.

[11] 4,141,883

[45] * Feb. 27, 1979

[54] STABILIZATION OF SYNTHETIC POLYMERS BY PENTA-OR-HEXA-SUBSTITUTED 4-PIPERIDINOL DERIVATIVES

[75] Inventors: Nobuo Soma; Tomoyuki Kurumada, both of Hiromachi, Japan; Heimo Brunetti, Reinach; Jean Rody, Basel, both of Switzerland

[73] Assignees: Sankyo Company, Limited, Tokyo, Japan; Ciba-Geigy Corporation, Ardsley, N.Y.

[*] Notice: The portion of the term of this patent subsequent to Feb. 21, 1995, has been disclaimed.

[21] Appl. No.: 813,927

[22] Filed: Jul. 8, 1977

Related U.S. Application Data

[63] Continuation-in-part of Ser. No. 687,793, May 19, 1976, Pat. No. 4,079,165.

[30] Foreign Application Priority Data

May 28, 1975 [JP] Japan .................................. 50-63850

[51] Int. Cl.$^2$ .................... C07D 211/6; C08K 5/34
[52] U.S. Cl. .................... 260/45.8 N; 542/401; 542/413; 542/426; 542/427; 544/130; 544/219; 544/70; 546/16; 546/25; 546/187; 546/188; 546/13; 546/14; 546/208; 546/193; 546/194; 546/205; 546/212; 546/213; 546/214; 546/207; 546/222; 546/221; 546/216; 546/242
[58] Field of Search .................................. 260/45.8 N

[56] References Cited

U.S. PATENT DOCUMENTS

| | | | |
|---|---|---|---|
| 3,640,928 | 2/1972 | Murayama et al. | 260/23 H |
| 3,705,166 | 12/1972 | Murayama et al. | 260/45.8 N |
| 3,840,494 | 10/1974 | Murayama et al. | 260/45.8 N |
| 3,984,371 | 10/1976 | Murayama et al. | 260/45.75 F |
| 3,992,390 | 11/1976 | Holt et al. | 260/45.8 N |
| 4,014,887 | 3/1977 | Randell et al. | 260/45.8 N |
| 4,021,432 | 5/1977 | Holt et al. | 260/45.8 N |
| 4,031,095 | 6/1977 | Ramey et al. | 260/45.8 N |
| 4,038,280 | 7/1977 | Randell et al. | 260/45.8 N |
| 4,046,737 | 9/1977 | Holt et al. | 260/45.8 N |
| 4,075,165 | 2/1978 | Soma et al. | 260/45.8 N |

*Primary Examiner*—Ronald W. Griffin
*Attorney, Agent, or Firm*—Vincent J. Cavalieri

[57] ABSTRACT

Polymers, both natural and synthetic, are stabilized against the deterioration resulting from heat and/or light by the incorporation of certain 2,2,6,6-tetra-substituted-4-piperidinol derivatives which additionally have an alkyl, alkenyl, alkynyl or aralkyl substituent at one or both of the 3- and 5- positions.

16 Claims, No Drawings

STABILIZATION OF SYNTHETIC POLYMERS BY PENTA-OR-HEXA-SUBSTITUTED 4-PIPERIDINOL DERIVATIVES

BACKGROUND OF THE INVENTION

This application is a continuation-in-part of the copending application Ser. No. 687,793 filed May 19, 1976, now U.S. Pat. No. 4,075,165, issued Feb. 21, 1978.

The present invention relates to a stabilized polymeric composition wherein the stabilizer comprises a 2,2,6,6-tetra-substituted-4-piperidinol derivative which is additionally substituted at one or both of the 3- and 5-positions.

4-Piperidinol derivatives are a known class of polymer stabilizers. For example, German Offenlegungsschrift No. 1,929,928 discloses compounds having the general formula:

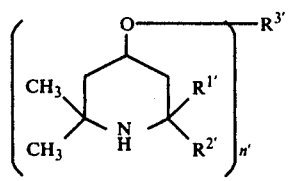

wherein:

$R^{1'}$ and $R^{2'}$ are the same or different and each represents an alkyl group or $R^{1'}$ and $R^{2'}$ form, together with the carbon atom to which they are attached, a saturated alicyclic group having from 5 to 7 ring carbon atoms or a group of the formula:

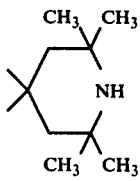

n' is an integer of from 1 to 3 inclusive; and when n' = 1:

$R^{3'}$ represents an acyl group, an N-substituted carbamoyl group, an N-substituted thiocarbamoyl group, a monovalent group obtained by removing a hydroxy group from an oxyacid, an alkyl group, a cycloalkyl group, an aralkyl group, an aryl group or a group of the formula:

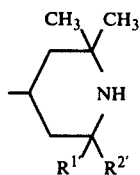

(wherein $R^{1'}$ and $R^{2'}$ are as defined above);

when n' = 2: $R^{3'}$ represents a diacyl group, a dicarbamoyl group, a bisthiocarbamoyl group, a carbonyl group, a divalent group obtained by removing two hydroxy groups from an oxyacid, an alkylene group, an arylene group or an arylenedialkylene group; and when n' = 3: $R^{3'}$ represents a triacyl group, a tricarbamoyl group, a tristhiocarbamoyl group, a trivalent group obtained by removing three hydroxy groups from an oxyacid, an alkanetriyl group, an arylenetriyl group or an arylenetriyltrialkylene group.

Moreover, German Offenlegungsschriften No. 2,204,659 and No. 2,258,752 disclose esters, carbamates and ethers having the above general formula except that the nitrogen atom in the piperidine ring is substituted with an alkyl, substituted alkyl, alkenyl, alkynyl, aralkyl or acyl group. Additionally, German Offenlegungsschrift No. 2,257,997 discloses, for example, the 4-hydroxy-3,5-di-t-butylphenylpropionate of 2,2,6,6-tetramethyl-4-piperidinol; German Offenlegungsschrift No. 2,319,816 discloses 2,4,6-tris(piperidyl-4-oxy)-1,3,5-triazine derivatives; and German Offenlegungsschrift No. 2,352,606 discloses β-(2,2,6,6-tetramethyl-4-piperidyloxy)-acrylate derivatives. All of these compounds are known to be effective stabilizers of polymeric materials, particularly of synthetic polymers.

SUMMARY OF THE INVENTION

It is an object of the present invention to provide stabilized polymer compositions comprising at least one polymer and at least one stabilizer which is a 3- and/or 5-substituted-2,2,6,6-tetra-substituted-4-piperidinol derivative and/or an acid addition salt thereof, in an amount sufficient to prevent photo- and thermal- deterioration.

The 4-piperidinol derivatives employed as stabilizers in the composition of the invention are compounds having the general formula (I):

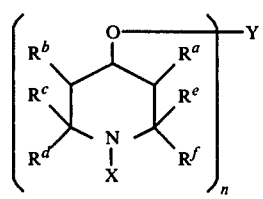

wherein:

$R^a$ and $R^b$ are the same or different and each represents a hydrogen atom, a lower alkyl group, an alkenyl group, an alkynyl group or an aralkyl group, provided that $R^a$ and $R^b$ do not simultaneously represent hydrogen atoms;

$R^c$ and $R^d$ are the same or different and each represents a lower alkyl group;

$R^3$ represents an alkyl group;

$R^f$ represents an alkyl group, a phenyl group, an aralkyl group or a 5- or 6- membered aromatic heterocyclic group containing an oxygen, sulphur or nitrogen atom; or $R^e$ and $R^f$, together with the carbon atom to which they are attached, represent a cycloalkyl group or a group of the formula:

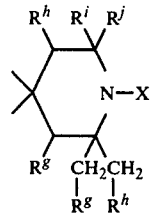

(wherein $R^g$ and $R^h$ are the same or different and each represents a hydrogen atom or a lower alkyl group, provided that $R^h$ does not represent a hydrogen atom when $R^g$ represents a lower alkyl group; $R^i$ and $R^j$ are the same or different and each represents a lower alkyl group; and X is as hereafter defined):

X represents a hydrogen atom, an oxyl radical, an alkyl group, an alkenyl group, an alkoxyalkyl group, an aralkyl group, which is unsubstituted or which has one or more substituents in its aryl moiety, a 2,3-epoxypropyl group, a group of formula —CH$_2$COOR$^1$ (wherein R$^1$ represents an alkyl group, an alkenyl group, a phenyl group, an aralkyl group or a cyclohexyl group), a group of formula:

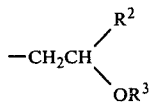

(wherein R$^2$ represents a hydrogen atom, a methyl group or a phenyl group and R$^3$ represents a hydrogen atom or an acyl group), an aliphatic acyl group or a group of formula —COOR$^4$ (wherein R$^4$ represents an alkyl group, a benzyl group or a phenyl group);

Y represents an organic or inorganic group or atom having a valency of from 1 to 4 and having essentially no adverse effect on the polymer stabilization activity; and n is an integer of from 1 to 4 inclusive.

In accordance with the invention, it has now been discovered that the 4-piperidinol derivatives of formula (I) or mixtures thereof and/or acid addition salts thereof can effectively stabilize a wide range of polymers against photo- and thermal-deterioration and have superior compatibility with polymers, particularly olefin polymers. The 4-piperidinol derivatives (I) may readily be incorporated into the polymer by conventional techniques at any convenient stage.

In this Specification, the term "lower alkyl" means alkyl having up to 6 carbon atoms.

DESCRIPTION OF PREFERRED EMBODIMENTS

In formula (I) when $R^a$ and/or $R^b$ represents a lower alkyl group, it may suitably be a lower alkyl group having from 1 to 4 carbon atoms, e.g. methyl, ethyl, propyl, isopropyl, butyl or isobutyl. When $R^a$ and/or $R^b$ represents an alkenyl group, it may suitably be one having 3 or 4 carbon atoms, e.g. allyl or 2-butenyl, especially allyl. When $R^a$ and/or $R^b$ represents an alkynyl group, it may suitably be one having 3 or 4 carbon atoms, e.g. propargyl or 2-butynyl, especially propargyl. When $R^a$ and/or $R^b$ represents an aralkyl group, it may suitably be one having 7 or 8 carbon atoms, e.g. a benzyl or phenethyl group.

$R^c$ and $R^d$ in formula (I) each represents a lower alkyl group and suitably one having from 1 to 5 carbon atoms, e.g. methyl, ethyl, propyl, butyl, isobutyl, pentyl or isopentyl.

When $R^e$ and/or $R^f$ represents an alkyl group, it may suitably be one having from 1 to 9 carbon atoms, e.g. methyl, ethyl, propyl, butyl, isobutyl, pentyl, isopentyl, hexyl, 3-methylhexyl or nonyl, most especially an alkyl group having from 1 to 5 carbon atoms. When $R^f$ represents an aralkyl group, it may suitably be one having 7 or 8 carbon atoms, e.g. benzyl or phenethyl. When $R^f$ represents a 5- or 6- membered aromatic heterocyclic group, it is preferably o-pyridyl, m-pyridyl, p-pyridyl, 2-furyl or 2-thienyl. Alternatively, $R^e$ and $R^f$, together with the carbon atom to which they are attached, may represent a cycloalkyl group, particularly a cycloalkyl group having from 5 to 7 carbon atoms (e.g. cyclopentyl, cyclohexyl or cycloheptyl, especially cyclohexyl) or a substituted piperidinyl group, e.g.:

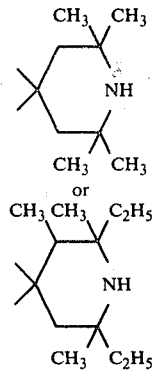

When X represents an alkyl group, it may suitably be an alkyl group having from 1 to 8 carbon atoms, e.g. methyl, ethyl, propyl, butyl, hexyl or octyl; however, in this case X preferably represents an alkyl group having from 1 to 4 carbon atoms, most especially a methyl group.

When X represents an alkenyl group, it may be an alkenyl group having from 3 to 6 carbon atoms, e.g. allyl, 2-butenyl or 2-hexenyl, and is more preferably an alkenyl group having 3 or 4 carbon atoms, most preferably an allyl group.

When X represents an alkoxyalkyl group, it may suitably be one having from 1 to 3 carbon atoms in its alkyl moiety and from 1 to 18 carbon atoms in its alkoxy moiety, e.g. methoxymethyl, ethoxymethyl, 2-methoxyethyl, 2-ethoxyethyl, 2-butoxyethyl, 3-butoxypropyl, 2-octoxyethyl or 2-octadecyloxyethyl, and is more preferably an alkoxyalkyl group containing a total of from 2 to 6 carbon atoms.

When X represents an aralkyl group, it may suitably by an aralkyl group having 7 or 8 carbon atoms, which is unsubstituted or has up to 3 substituents in its aryl moiety; the substituents may be the same or different and examples are chlorine atoms, alkyl groups having from 1 to 4 carbon atoms, alkoxy groups having from 1 to 8 carbon atoms and hydroxy groups. Examples of the group X, when X represents an aralkyl group, are thus: benzyl, phenethyl, o-chlorobenzyl, m-chlorobenzyl, p-chlorobenzyl, o-methylbenzyl, m-methylbenzyl, p-methylbenzyl, p-isopropylbenzyl, p-t-butylbenzyl, p-methoxybenzyl, p-butoxybenzyl, p-octoxybenzyl or 4-hydroxy-3,5-di-t-butylbenzyl; of these, benzyl itself is preferred.

When X represents a group of the formula —CH$_2$COOR$^1$, R$^1$ represents an alkyl group, preferably having from 1 to 18 carbon atoms (e.g. a methyl, ethyl, isopropyl, butyl, isobutyl, t-butyl, isopentyl, octyl, dodecyl or octadecyl group), an alkenyl group, preferably having from 3 to 6 carbon atoms (e.g. an allyl, 2-butenyl or 2-hexenyl group), a phenyl group, an aralkyl group, preferably having 7 or 8 carbon atoms (e.g. a benzyl or phenethyl group) or a cyclohexyl group; of these, we prefer an alkyl group having from 1 to 4 carbon atoms.

When X represents a group of formula:

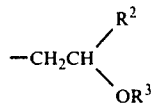

$R^2$ represents a hydrogen atom, a methyl group or a phenyl group, and $R^3$ represents a hydrogen atom or an acyl group, e.g. an aliphatic, araliphatic, aromatic or alicyclic acyl group. The acyl group is preferably a group of formula $—COR^{15}$, in which $R^{15}$ represents an alkyl group having from 1 to 17 carbon atoms (e.g. a methyl, ethyl, propyl, isopropyl, butyl, heptyl, 1-ethylpentyl, nonyl, undecyl or heptadecyl group), an alkenyl group having from 2 to 4 carbon atoms (e.g. a vinyl, 1-propenyl, isopropenyl, 2-methyl-1-propenyl or 1-butenyl group), a phenyl group, which is unsubstituted or has up to 3 chlorine, $C_{1-4}$ alkyl, $C_{1-8}$ alkoxy or hydroxy substituents, the substituents being the same or different, (e.g. phenyl itself, o-chlorophenyl, m-chlorophenyl, p-chlorophenyl, 2,4-dichlorophenyl, o-methylphenyl, m-methylphenyl, p-methylphenyl, p-isopropylphenyl, p-t-butylphenyl, p-methoxyphenyl, p-ethoxyphenyl, p-butoxyphenyl, p-octoxyphenyl, 3,4,5-trimethoxyphenyl, o-hydroxyphenyl or 4-hydroxy-3,5-di-t-butylphenyl), an aralkyl group having 7 or 8 carbon atoms, which is unsubstituted or has up to 3 chlorine, $C_{1-4}$ alkyl, $C_{1-8}$ alkoxy or hydroxy substituents in its aryl moiety, the substituents being the same or different (e.g. benzyl, phenethyl, p-methylbenzyl or 4-hydroxy-3,5-di-t-butylphenethyl), a styryl group or a cyclohexyl group. Of these groups represented by X, we particularly prefer a group of formula $—CH_2CH_2.OR^3$ (in which $R^3$ is as defined above).

When X represents an aliphatic acyl group, it may suitably be one having up to 4 carbon atoms and is preferably a lower alkanoyl or alkenoyl group, e.g. a formyl, acetyl, acryloyl or crotonoyl group.

When X represents a group of the formula $—COOR^4$, $R^4$ represents an alkyl group, preferably having from 1 to 8 carbon atoms (e.g. methyl, ethyl, isobutyl or octyl), a benzyl group or a phenyl group.

The nature of the group Y is relatively less important, provided that it does not adversely affect the polymer stabilization activity of the 4-piperidinol derivative (I); such groups are well-known to those skilled in the art. In general, the group Y preferably represents a hydrogen atom, a hydrocarbon residue, which may be substituted or unsubstituted, a residue derived from an organic or inorganic acid by splitting off at least one hydroxy group from the acid, a heterocyclic group or a phosphorus, boron or silicon atom. In particular, the following groups are preferred:

When n = 1;

Y preferably represents: a hydrogen atom; an aliphatic, araliphatic, alicyclic, aromatic or heterocyclic acyl group, preferably an acyl group having up to 18 carbon atoms and more preferably a group of formula $—COR^{16}$, in which $R^{16}$ represents a hydrogen atom, an alkyl group having from 1 to 17 carbon atoms (e.g. a methyl, ethyl, propyl, isopropyl, butyl, t-butyl, pentyl, isopentyl, 1-ethylpentyl, nonyl, undecyl, pentadecyl or heptadecyl group), an alkenyl group having from 2 to 5 carbon atoms (e.g. a vinyl, 1-propenyl, 2-methyl-1-propenyl, isopropenyl or 1,3-pentadienyl group), an alkynyl group having 2 or 3 carbon atoms (e.g. an ethynyl or 1-propynyl group), a phenyl group which is unsubstituted or has up to 3 chlorine, $C_{1-4}$ alkyl, $C_{1-8}$ alkoxy, hydroxy or nitro substituents, the substituents being the same or different, (e.g. phenyl, o-chlorophenyl, m-chlorophenyl, p-chlorophenyl, o-methylphenyl, m-methylphenyl, p-methylphenyl, p-isopropylphenyl, p-t-butylphenyl, m-methoxyphenyl, p-methoxyphenyl, p-butoxyphenyl, p-octoxyphenyl, o-hydroxyphenyl, 2-hydroxy-3-methylphenyl, 2-hydroxy-4-methylphenyl, 4-hydroxy-3,5-di-t-butylphenyl or m-nitrophenyl), a naphthyl group, a styryl group, an aralkyl group having 7 or 8 carbon atoms which may be unsubstituted or have up to 3 chlorine, $C_{1-4}$ alkyl, $C_{1-8}$ alkoxy or hydroxy substituents, the substituents being the same or different, (e.g. a benzyl, phenethyl, 4-hydroxy-3,5-di-t-butylbenzyl or 4-hydroxy-3,5-di-t-butylphenethyl group), a phenoxymethyl group, a cyclohexyl group, a 2-pyridyl group, a 3-pyridyl group, a 4-pyridyl group, a 2-furyl group or a 2-thienyl group;

a group of formula $—CO.R^5.COOH$ [in which $R^5$ represents an alkylene group, preferably having from 1 to 10 carbon atoms, whose chain may optionally be interrupted by a sulphur atom (e.g. an ethylene, tetramethylene, octamethylene, decamethylene or 3-thiapentamethylene group) or a phenylene group (o-phenylene, m-phenylene or p-phenylene)] or a metal salt (the metal being, for example, barium, nickel, manganese, calcium, zinc, iron, sodium, cobalt or tin) or lower alkyl ester (preferably having from 1 to 4 carbon atoms in the alkyl group, e.g. a methyl, ethyl, propyl, isopropyl or butyl ester) thereof;

a monovalent group obtained by removing a hydroxy group from a sulphur-containing acid, for example a group of formula $—SO_2.R^6$, in which $R^6$ represents a lower alkyl group, preferably having from 1 to 3 carbon atoms (e.g. a methyl, ethyl or propyl group), a phenyl group or a tolyl group;

a group obtained by removing a hydroxy group from a phosphorus-containing acid, e.g. a substituted or unsubstituted phosphoric, phosphonic or phosphorous acid, particularly a group of formula:

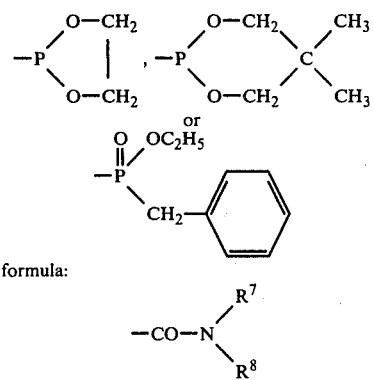

a group of formula:

$$-CO-N\begin{matrix}R^7\\R^8\end{matrix}$$

in which $R^7$ represents a hydrogen atom, a lower alkyl group (preferably having from 1 to 4 carbon atoms, e.g. a methyl, ethyl, propyl or butyl group), an aralkyl group (preferably having 7 or 8 carbon atoms, e.g. a benzyl or phenethyl group) or phenyl group, and $R^8$ represents an alkyl group (preferably having from 1 to 18 carbon atoms, e.g. a methyl, ethyl, propyl, butyl, dodecyl or octadecyl group), an aryl group (preferably having from 6 to 10 carbon atoms) which may be unsubstituted or substituted, preferably by one or more chlorine atoms and/or $C_{1-4}$ alkyl groups (for example, a phenyl, o-chlorophenyl, m-chlorophenyl, p-chlorophenyl, o-tolyl, m-tolyl, p-tolyl, α-naphthyl or β-naphthyl group), an aralkyl group (preferably having 7 or 8 carbon atoms, e.g. a benzyl or phenethyl group) or a cyclohexyl group, or $R^7$ and $R^8$, together with the nitrogen atom to which they are attached, represent a piperidino group, a 1-pyrrolidinyl group or a morpholino group; particularly preferred amongst such groups are those of formula —CO.NHR$^8$ (in which $R^8$ is as defined above);

an alkyl group, preferably an alkyl group having from 1 to 18 carbon atoms (e.g. a methyl, ethyl, butyl, isobutyl, octyl, dodecyl or octadecyl group);

an alkenyl group, preferably an alkenyl group having from 3 to 6 carbon atoms (e.g. an allyl, 2-butenyl, methallyl or 2-hexenyl group);

an aralkyl group, which is unsubstituted or has one or more substituents in its aryl moiety, preferably an aralkyl group having from 7 to 9 carbon atoms and optionally having up to 3 $C_{1-4}$ alkyl and/or hydroxy substituents in its aryl moiety [e.g. a benzyl, phenethyl, p-methylbenzyl, p-isopropylbenzyl, 4-hydroxy-3,5-di-t-butylbenzyl or 3-(4-hydroxy-3,5-di-t-butylphenyl)propyl group, most preferably a benzyl group];

a cyclohexyl group; or a group having the formula:

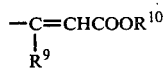

(in which $R^9$ represents a hydrogen atom, a methyl group or a phenyl group and $R^{10}$ represents an alkyl group, preferably an alkyl group having from 1 to 8 carbon atoms), for example a 2-ethoxycarbonylethenyl, a 2-methoxycarbonylisopropenyl, a 2-octoxycarbonylethenyl or a 2-ethoxycarbonyl-1-phenylethenyl group;

When n = 2:

Y preferably represents an aliphatic, araliphatic, aromatic, alicyclic or heterocyclic diacyl group, preferably having up to 12 carbon atoms and preferably a group of the formula —CO.($R^{17}$)$_m$.CO-, in which m is 0 or 1 and $R^{17}$ represents an alkylene group having from 1 to 10 carbon atoms, the chain of which may optionally be interrupted by a sulphur atom (e.g. a methylene, ethylene, tetramethylene, hexamethylene, octamethylene, decamethylene or 3-thiapentamethylene group), an alkenylene group having from 2 to 4 carbon atoms (e.g. vinylene, 2-butenylene or 1,2-prop-2-enylene), a phenylene group (o-phenylene, m-phenylene or p-phenylene), a cyclohexylene group (e.g. a 1,4-cyclohexylene group), a 2,4-pyridinediyl group, a 2,5-pyridinediyl group or a 2,5-thiophenediyl group;

a carbonyl group;

a sulphinyl group;

a sulphonyl group;

a group obtained by removing two hydroxy groups from a phosphorus-containing acid, particularly a group of formula:

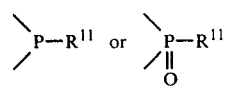

in which $R^{11}$ represents a hydrogen atom, a lower alkyl group (preferably having from 1 to 4 carbon atoms, e.g. a methyl, ethyl, propyl or butyl group) or a substituted or unsubstituted phenyl or benzyl group (e.g. a phenyl group, a benzyl group or a 4-hydroxy-3,5-di-t-butylbenzyl group);

a group of formula:

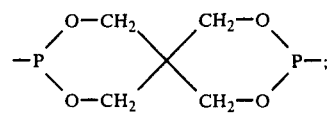

a group of formula:

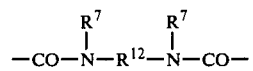

in which $R^7$ is as defined above and $R^{12}$ represents an alkylene group (preferably having from 2 to 10 carbon atoms, e.g. an ethylene, tetramethylene, hexamethylene or decamethylene group), an arylene group preferably having from 6 to 10 carbon atoms and optionally having one or more methyl substituents (e.g. an o-phenylene, m-phenylene, p-phenylene, 2,4-tolylene or 1,5-naphthylene group), a xylylene group (e.g. a m-xylylene or p-xylylene group), a cyclohexylene group (e.g. a 1,4-cyclohexylene group), a group of formula:

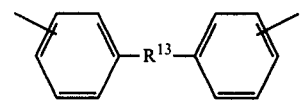

(in which $R^{13}$ represents an oxygen atom or a methylene group, for example an oxydi-p-phenylene or methylenedi-p-phenylene group), a group of formula:

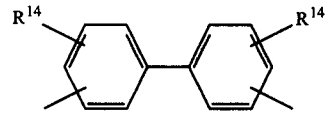

(in which $R^{14}$ represents a hydrogen atom or a methyl group, for example a p,p'-diphenylene or 3,3'-dimethyl-4,4'-diphenylene group), a group having the formula:

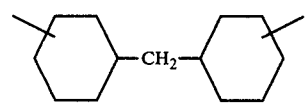

(e.g. methylene-di-4,1-cyclohexylene), or a group having the formula:

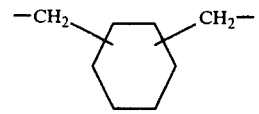

(e.g. 1,3-cyclohexylenedimethylene or 1,4-cyclohexylenedimethylene); of these groups, we particularly prefer those groups of formula —CO.NH.R$^{12}$.NH.CO—(in which $R^{12}$ is as defined above);

an alkylene group, preferably having from 1 to 10 carbon atoms (e.g. a methylene, ethylene, tetramethylene, hexamethylene, 2-ethyl-1,3-hexylene or decamethylene group), more preferably an alkylene group having from 2 to 6 carbon atoms;

an alkenylene group, preferably having from 4 to 10 carbon atoms (e.g. 2-butenylene); a xylylene group (o-xylylene, m-xylylene or p-xylylene); or a group of the formula

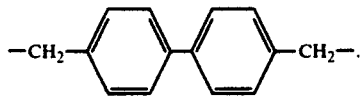

When n = 3:

Y preferably represents: a group having the formula

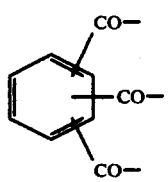

namely

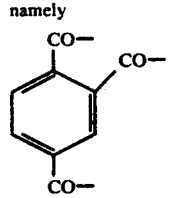 , 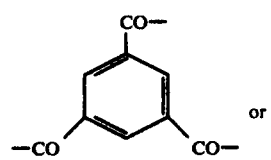 or

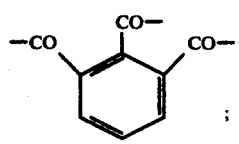

a group of formula

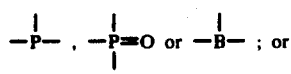

or a group of the formula

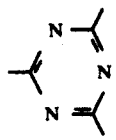

When n = 4:

Y preferably represents a group of the formula

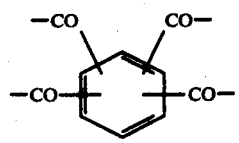

most especially a group of formula

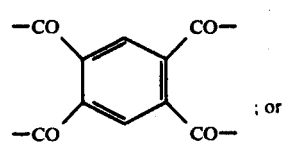 ; or a group of the formula

Particularly preferred compounds are those of formula

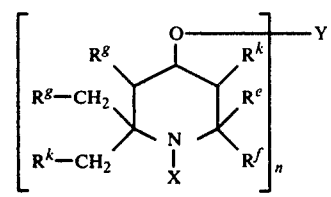

(wherein $R^e$, $R^f$, $R^g$, X, Y and n are as defined above and $R^k$ represents a lower alkyl group, preferably having from 1 to 4 carbon atoms). Within this preferred class of compounds, a more preferred class comprises those of formula:

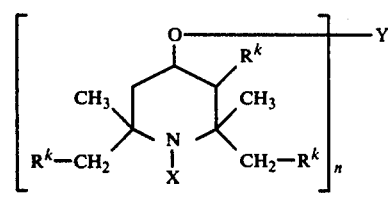

(in which $R^k$, X, Y and n are as defined above); of these, compounds in which Y is as defined above but other than hydrogen are more preferred.

Of the more preferred compounds above, the most preferred compounds have the general formula:

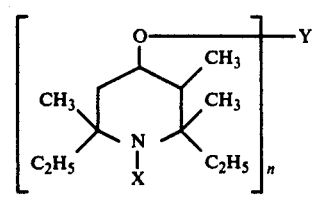

(in which X, Y and n are as defined above); of these, compounds in which Y is as defined above but other than hydrogen are more preferred.

The most preferred compounds are those in which:

$R^a$, $R^c$ and $R^e$ each represent methyl groups;

$R^b$ represents a hydrogen atom;

$R^d$ and $R^f$ each represent ethyl groups;

X represents a hydrogen atom, a methyl group, an allyl group, a benzyl group, a 2,3-epoxypropyl group or a group of formula —$CH_2CH_2OR^3$ (in which $R^3$ represents a hydrogen atom, an alkanoyl group having from 2 to 18 carbon atoms or a benzoyl group), most preferably a hydrogen atom or a methyl group;

n is 1, 2 or 3;

when n = 1:

Y represents a group of formula —$COR^{16}$ (wherein $R^{16}$ represents an alkyl group having from 1 to 17 carbon atoms, a phenyl group which is optionally substituted by up to three $C_{1-4}$ alkyl and/or hydroxy substituents, or a 4-hydroxy-3,5-di-t-butylphenethyl group) or a group of formula —CO—NHR$^8$ (wherein R$^8$ represents an alkyl group having from 1 to 18 carbon atoms, a phenyl group or a cyclohexyl group); and when n = 2:

Y represents a group of formula —CO.(R$^{17}$)$_m$.CO— (wherein m is 0 or 1 and R$^{17}$ represents an alkylene group having from 1 to 10 carbon atoms, the group —CH$_2$CH$_2$SCH$_2$CH$_2$— or a phenylene group), a sulphinyl group or a group of formula —CO.NH.R$^{12}$.NH.CO— (wherein R$^{12}$ represents a hexamethylene group, a 2,4-tolylene group or a methylene-di-p-phenylene group).

Most especially preferred compounds are those in which n = 1 and Y represents a group of formula —COR$^{16}$ or n = 2 and Y represents a group of formula —CO.R$^{17}$.CO— (wherein R$^{16}$ and R$^{17}$ are as defined above).

The interested are compounds having a combination of X (in which it is a hydrogen atom, methyl, allyl, benzyl or 2,3-epoxypropyl group) with Y (in which it is a group of formula —COR$^{16}$ or —CO.R$^{17}$.CO—, and R$^{16}$ is C$_{1-17}$ alkyl or phenyl and R$^{17}$ is C$_{1-10}$ alkylene).

A single one of the 4-piperidinol derivatives (I) and /or acid addition salts thereof may be employed as the stabilizer in the polymeric composition of the present invention. Alternatively, a mixture of two or more such 4-piperidinol derivatives and/or acid addition salts thereof may be employed. In particular, it is possible to use a mixture of the 3- and 5-positional isomers of the 4-piperidinol derivatives. Additionally, since the 4-piperidinol derivatives (I) exist in the form of various stereoisomers, it is possible to use a mixture of these stereoisomers. If desired, however, at any stage during the synthesis of the 4-piperidinol derivatives, the mixture of isomers usually obtained can be separated by known methods.

Acid addition salts of the 4-piperidinol derivatives (I) are also effective stabilizers and may be employed in the polymeric compositions of the invention. The nature of the acid used in such acid addition salts is not critical, provided that it does not adversely affect the stability of the polymer to be stabilized. Examples of suitable acids are: inorganic acids, such as sulphuric acid, hydrochloric acid and phosphoric acid; organic carboxylic acids, such as formic acid, acetic acid, valeric acid, stearic acid, oxalic acid, adipic acid, sebacic acid, maleic acid, benzoic acid, p-t-butylbenzoic acid, 4-hydroxy-3,5-di-t-butylbenzoic acid, salicylic acid and terephthalic acid; sulphonic acids, such as methanesulphonic acid and p-toluenesulphonic acid; or organic phosphonic acids such as phenylphosphonic acid. Of these, the organic carboxylic acids are most preferred.

The following is a non-limiting list of individual 4-piperidinol derivatives of formula (I). The numbers appended to the compounds in this list will be used to identify them hereinafter in the Examples.

Having regard to their activity, ease of preparation and compatibility with polymers, those 4-piperidinol derivatives (I) which are esters are particularly preferred. The most preferred compounds are Compounds Nos. 5, 7, 10, 11, 17, 43, 50, 54. 64, 163, 166 and 210 identified in the following list, and acid addition salts thereof.

1. 2,6-diethyl-2,3,6-trimethyl-4-piperidinol.
2. 2,6-diethyl-2,3,6-trimethyl-4-piperidyl acetate.
3. 2,6-diethyl-2,3,6-trimethyl-4-piperidyl pivalate.
4. 2,6-diethyl-2,3,6-trimethyl-4-piperidyl 2-ethylhexanoate.
5. 2,6-diethyl-2,3,6-trimethyl-4-piperidyl stearate.
6. 2,6-diethyl-2,3,6-trimethyl-4-piperidyl acrylate.
7. 2,6-diethyl-2,3,6-trimethyl-4-piperidyl crotonate.
8. 2,6-diethyl-2,3,6-trimethyl-4-piperidyl methacrylate.
9. 2,6-diethyl-2,3,6-trimethyl-4-piperidyl tetrolate (=methylacetylenecarboxylate).
10. 2,6-diethyl-2,3,6-trimethyl-4-piperidyl benzoate.
11. 2,6-diethyl-2,3,6-trimethyl-4-piperidyl p-t-butylbenzoate.
12. 2,6-diethyl-2,3,6-trimethyl-4-piperidyl p-methoxybenzoate.
13. 2,6-diethyl-2,3,6-trimethyl-4-piperidyl salicylate.
14. 2,6-diethyl-2,3,6-trimethyl-4-piperidyl p-chlorobenzoate.
15. 2,6-diethyl-2,3,6-trimethyl-4-piperidyl naphthalene-1-carboxylate.
16. 2,6-diethyl-2,3,6-trimethyl-4-piperidyl phenylacetate.
17. 2,6-diethyl-2,3,6-trimethyl-4-piperidyl β-(4-hydroxy-3,5-di-t-butylphenyl)propionate.
18. 2,6-diethyl-2,3,6-trimethyl-4-piperidyl cinnamate.
19. 2,6-diethyl-2,3,6-trimethyl-4-piperidyl cyclohexanecarboxylate.
20. 2,6-diethyl-2,3,6-trimethyl-4-piperidyl methyl sebacate.
21. 2,6-diethyl-2,3,6-trimethyl-4-piperidyl methyl phthalate.
22. 2,6-diethyl-2,3,6-trimethyl-4-piperidyl methanesulphonate.
23. 2,6-diethyl-2,3,6-trimethyl-4-piperidyl p-toluenesulphonate.
24. 4-acetoxy-2,6-diethyl-2,3,6-trimethylpiperidine-1-oxyl.
25. 4-benzoyloxy-2,6-diethyl-2,3,6-trimethylpiperidine-1-oxyl.
26. 2,6-diethyl-1,2,3,6-tetramethyl-4-piperidinol.
27. 2,6-diethyl-1,2,3,6-tetramethyl-4-piperidyl stearate.
28. 2,6-diethyl-1,2,3,6-tetramethyl-4-piperidyl benzoate.
29. 2,6-diethyl-1,2,3,6-tetramethyl-4-piperidyl m-toluate.
30. 2,6-diethyl-1,2,3,6-tetramethyl-4-piperidyl p-octyloxybenzoate.
31. 2,6-diethyl-1,2,3,6-tetramethyl-4-piperidyl β-(4-hydroxy-3,5-di-t-butylphenyl)propionate.
32. 2,6-diethyl-1,2,3,6-tetramethyl-4-piperidyl p-toluenesulphonate.
33. 1-butyl-2,6-diethyl-2,3,6-trimethyl-4-piperidyl hexanoate.
34. 1-allyl-2,6-diethyl-2,3,6-trimethyl-4-piperidyl stearate.
35. 1-allyl-2,6-diethyl-2,3,6-trimethyl-4-piperidyl crotonate.
36. 1-allyl-2,6-diethyl-2,3,6-trimethyl-4-piperidyl benzoate.
37. 1-benzyl-2,6-diethyl-2,3,6-trimethyl-4-piperidyl acetate.
38. 1-benzyl-2,6-diethyl-2,3,6-trimethyl-4-piperidyl stearate.
39. 1-benzyl-2,6-diethyl-2,3,6-trimethyl-4-piperidyl crotonate.
40. 1-benzyl-2,6-diethyl-2,3,6-trimethyl-4-piperidyl benzoate.
41. 2,6-diethyl-2,3,6-trimethyl-1-(4-methylbenzyl)-4-piperidyl benzoate.
42. 1-(2,3-epoxypropyl)-2,6-diethyl-2,3,6-trimethyl-4-piperidyl stearate.
43. 1-(2,3-epoxypropyl)-2,6-diethyl-2,3,6-trimethyl-4-piperidyl benzoate.

44. 2,6-diethyl-1-(2-hydroxyethyl)-2,3,6-trimethyl-4-piperidinol.
45. 2,6-diethyl-1-(2-hydroxyethyl)-2,3,6-trimethyl-4-piperidyl benzoate.
46. 2,6-diethyl-1-(2-hydroxypropyl)-2,3,6-trimethyl-4-piperidyl benzoate.
47. 2,6-diethyl-1-(2-hydroxy-2-phenylethyl)-2,3,6-trimethyl-4-piperidyl p-t-butylbenzoate.
48. 1-(2-acetoxyethyl)-2,6-diethyl-2,3,6-trimethyl-4-piperidyl butyrate.
49. 1-(2-acetoxyethyl)-2,6-diethyl-2,3,6-trimethyl-4-piperidyl crotonate.
50. 1-(2-acetoxyethyl)-2,6-diethyl-2,3,6-trimethyl-4-piperidyl benzoate.
51. 2,6-diethyl-2,3,6-trimethyl-1-(2-stearoyloxyethyl)-4-piperidyl stearate.
52. 1-(2-acryloyloxyethyl)-2,6-diethyl-2,3,6-trimethyl-4-piperidyl benzoate.
53. 2,6-diethyl-1-{2-[β-(4-hydroxy-3,5-di-t-butylphenyl)propionyloxy]ethyl}-2,3,6-trimethyl-4-piperidyl benzoate.
54. 1-(2-benzoyloxyethyl)-2,6-diethyl-2,3,6-trimethyl-4-piperidyl benzoate.
55. 1-(2-benzoyloxyethyl)-2,6-diethyl-2,3,6-trimethyl-4-piperidyl β-phenylpropionate.
56. 1-(2-acetoxypropyl)-2,6-diethyl-2,3,6-trimethyl-4-piperidyl benzoate.
57. 1-(2-benzoyloxypropyl)-2,6-diethyl-2,3,6-trimethyl-4-piperidyl butyrate.
58. 1-(2-acetoxy-2-phenylethyl)-2,6-diethyl-2,3,6-trimethyl-4-piperidyl benzoate.
59. 1-(ethoxycarbonylmethyl)-2,6-diethyl-2,3,6-trimethyl-4-piperidyl benzoate.
60. 1-(butoxycarbonylmethyl)-2,6-diethyl-2,3,6-trimethyl-4-piperidyl benzoate.
61. 1-ethoxymethyl-2,6-diethyl-2,3,6-trimethyl-4-piperidyl benzoate.
62. 1-butoxyethyl-2,6-diethyl-2,3,6-trimethyl-4-piperidyl benzoate.
63. 2,6-diethyl-1-formyl-2,3,6-trimethyl-4-piperidyl benzoate.
64. 1-acetyl-2,6-diethyl-2,3,6-trimethyl-4-piperidyl benzoate.
65. 1-crotonoyl-2,6-diethyl-2,3,6-trimethyl-4-piperidyl benzoate.
66. 2,6-diethyl-2,3,6-trimethyl-4-piperidyl methylcarbamate.
67. 2,6-diethyl-2,3,6-trimethyl-4-piperidyl ethylcarbamate.
68. 2,6-diethyl-2,3,6-trimethyl-4-piperidyl octadecylcarbamate.
69. 2,6-diethyl-2,3,6-trimethyl-4-piperidyl carbanilate.
70. 2,6-diethyl-2,3,6-trimethyl-4-piperidyl m-methylcarbanilate.
71. 2,6-diethyl-2,3,6-trimethyl-4-piperidyl p-chlorocarbanilate.
72. 2,6-diethyl-2,3,6-trimethyl-4-piperidyl 1-naphthalenecarbamate.
73. 2,6-diethyl-2,3,6-trimethyl-4-piperidyl cyclohexanecarbamate.
74. 2,6-diethyl-2,3,6-trimethyl-4-piperidyl piperidine-1-carboxylate.
75. 2,6-diethyl-2,3,6-trimethyl-4-piperidyl pyrrolidine-1-carboxylate.
76. 2,6-diethyl-2,3,6-trimethyl-4-methylcarbamoyloxypiperidine-1-oxyl.
77. 2,6-diethyl-1,2,3,6-tetramethyl-4-piperidyl methylcarbamate.
78. 2,6-diethyl-1,2,3,6-tetramethyl-4-piperidyl carbanilate.
79. 1-butyl-2,6-diethyl-2,3,6-trimethyl-4-piperidyl methylcarbamate.
80. 1-allyl-2,6-diethyl-2,3,6-trimethyl-4-piperidyl methylcarbamate.
81. 1-benzyl-2,6-diethyl-2,3,6-trimethyl-4-piperidyl methylcarbamate.
82. 1-benzyl-2,6-diethyl-2,3,6-trimethyl-4-piperidyl N-benzyl-N-methylcarbamate.
83. 1-benzyl-2,6-diethyl-2,3,6-trimethyl-4-piperidyl cyclohexanecarbamate.
84. 2,6-diethyl-1-(2-hydroxyethyl)-2,3,6-trimethyl-4-piperidyl methylcarbamate.
85. 1-(2-acetoxyethyl)-2,6-diethyl-2,3,6-trimethyl-4-piperidyl methylcarbamate.
86. 1-(2-acetoxyethyl)-2,6-diethyl-2,3,6-trimethyl-4-piperidyl carbanilate.
87. 2,6-diethyl-2,3,6-trimethyl-1-(2-stearoyloxyethyl)-4-piperidyl methylcarbamate.
88. 1-(2-benzoyloxyethyl)-2,6-diethyl-2,3,6-trimethyl-4-piperidyl carbanilate.
89. 1-(2,3-epoxypropyl)-2,6-diethyl-2,3,6-trimethyl-4-piperidyl methylcarbamate.
90. 1-(ethoxycarbonylmethyl)-2,6-diethyl-2,3,6-trimethyl-4-piperidyl methylcarbamate.
91. 2,6-diethyl-4-methoxy-2,3,6-trimethylpiperidine.
92. 4-butoxy-2,6-diethyl-2,3,6-trimethylpiperidine.
93. 2,6-diethyl-2,3,6-trimethyl-4-octadecyloxypiperidine.
94. 4-cyclohexyloxy-2,6-diethyl-2,3,6-trimethylpiperidine.
95. 4-benzyloxy-2,6-diethyl-2,3,6-trimethylpiperidine.
96. ethyl β-(2,6-diethyl-2,3,6-trimethyl-4-piperidyloxy)acrylate.
97. methyl β-(2,6-diethyl-2,3,6-trimethyl-4-piperidyloxy)crotonate.
98. 4-benzyloxy-2,6-diethyl-2,3,6-trimethylpiperidine-1-oxyl.
99. 2,6-diethyl-4-methoxy-1,2,3,6-tetramethylpiperidine.
100. 4-benzyloxy-2,6-diethyl-1,2,3,6-tetramethylpiperidine.
101. 1-allyl-2,6-diethyl-2,3,6-trimethyl-4-octadecyloxypiperidine.
102. 1-allyl-4-allyloxy-2,6-diethyl-2,3,6-trimethylpiperidine.
103. 1-benzyl-2,6-diethyl-4-methoxy-2,3,6-trimethylpiperidine.
104. 2,6-diethyl-1-(2-hydroxyethyl)-4-methoxy-2,3,6-trimethylpiperidine.
105. 1-(2-acetoxyethyl)-2,6-diethyl-4-methoxy-2,3,6-trimethylpiperidine.
106. 1-(2-benzoyloxyethyl)-4-benzoyloxy-2,6-diethyl-2,3,6-trimethylpiperidine.
107. 2,2,6,6-tetraethyl-3,5-dimethyl-4-piperidinol.
108. 2,2,6,6-tetraethyl-3,5-dimethyl-4-piperidyl hexanoate.
109. 2,2,6,6-tetraethyl-3,5-dimethyl-4-piperidyl benzoate.
110. 2,2,6,6-tetraethyl-3,5-dimethyl-4-piperidyl m-nitrobenzoate.
111. 2,2,6,6-tetraethyl-1,3,5-trimethyl-4-piperidyl benzoate.
112. 1-benzyl-2,2,6,6-tetraethyl-3,5-dimethyl-4-piperidyl benzoate.
113. 2,2,6,6-tetraethyl-3,5-dimethyl-4-piperidyl carbanilate.

114. 2,6-diisobutyl-3-isopropyl-2,6-dimethyl-4-piperidinol.
115. 2,6-diisobutyl-3-isopropyl-2,6-dimethyl-4-piperidyl acetate.
116. 2,6-diisobutyl-3-isopropyl-2,6-dimethyl-4-piperidyl stearate.
117. 2,6-diisobutyl-3-isopropyl-2,6-dimethyl-4-piperidyl acrylate.
118. 2,6-diisobutyl-3-isopropyl-2,6-dimethyl-4-piperidyl benzoate.
119. 2,6-diisobutyl-3-isopropyl-1,2,6-trimethyl-4-piperidyl benzoate.
120. 1-allyl-2,6-diisobutyl-3-isopropyl-2,6-dimethyl-4-piperidyl benzoate.
121. 1-benzyl-2,6-diisobutyl-3-isopropyl-2,6-dimethyl-4-piperidyl benzoate.
122. 1-(2-acetoxyethyl)-2,6-diisobutyl-3-isopropyl-2,6-dimethyl-4-piperidyl p-t-butylbenzoate.
123. 2,6-diisobutyl-3-isopropyl-2,6-dimethyl-4-piperidyl methylcarbamate.
124. 2,6-diisobutyl-3-isopropyl-2,6-dimethyl-4-piperidyl carbanilate.
125. 3-isobutyl-2,6-diisopentyl-2,6-dimethyl-4-piperidinol.
126. 3-isobutyl-2,6-diisopentyl-2,6-dimethyl-4-piperidyl benzoate.
127. 3-isobutyl-2,6-diisopentyl-1,2,6-trimethyl-4-piperidyl benzoate.
128. 3-isobutyl-2,6-diisopentyl-2,6-dimethyl-4-piperidyl butylcarbamate.
129. 4-ethoxy-3-isobutyl-2,6-diisopentyl-2,6-dimethylpiperidine.
130. 6-ethyl-2,2,3,6-tetramethyl-4-piperidyl benzoate.
131. 6-ethyl-1,2,2,3,6-pentamethyl-4-piperidyl p-t-butylbenzoate.
132. 6-ethyl-2,3,6-trimethyl-2-nonyl-4-piperidinol.
133. 6-ethyl-2,3,6-trimethyl-2-nonyl-4-piperidyl p-t-butylbenzoate.
134. 2,2-dibutyl-6-ethyl-3,6-dimethyl-4-piperidyl benzoate.
135. 6-ethyl-2,3,6-trimethyl-2-phenethyl-4-piperidinol.
136. 6-ethyl-2,3,6-trimethyl-2-phenethyl-4-piperidyl valerate.
137. 6-ethyl-2,3,6-trimethyl-2-phenethyl-4-piperidyl p-t-butylbenzoate.
138. 6-ethyl-2,3,6-trimethyl-2-phenethyl-4-piperidyl methylcarbamate.
139. 6-ethyl-2,3,6-trimethyl-2-phenyl-4-piperidyl stearate.
140. 6-ethyl-2,3,6-trimethyl-2-phenyl-4-piperidyl benzoate.
141. 6-ethyl-1,2,3,6-tetramethyl-2-phenyl-4-piperidyl benzoate.
142. 6-ethyl-2,3,6-trimethyl-2-phenyl-4-piperidyl methylcarbamate.
143. 6-ethyl-4-methoxy-2,3,6-trimethyl-2-phenylpiperidine.
144. 6-ethyl-2,3,6-trimethyl-2-(3-pyridyl)-4-piperidinol.
145. 6-ethyl-2,3,6-trimethyl-2-(3-pyridyl)-4-piperidyl benzoate.
146. 6-ethyl-2-(2-furyl)-2,3,6-trimethyl-4-piperidyl benzoate.
147. 2-ethyl-2,5-dimethyl-1-azaspiro[5.5]undecan-4-ol.
148. 2-ethyl-2,5-dimethyl-1-azaspiro[5.5]undec-4-yl stearate.
149. 2-ethyl-2,5-dimethyl-1-azaspiro[5.5]undec-4-yl benzoate.
150. 2-ethyl-2,5-dimethyl-1-azaspiro[5.5]undec-4-yl methylcarbamate.
151. 4-benzyloxy-2-ethyl-2,5-dimethyl-1-azaspiro[5.5]undecane.
152. 7-ethyl-7,10-dimethyl-6-azaspiro[4.5]dec-9-yl benzoate.
153. 7-ethyl-7,10-dimethyl-6-azaspiro[4.5]dec-9-yl N-benzyl-N-octadecylcarbamate.
154. 6-butyl-7-ethyl-9-methoxy-7,10-dimethyl-6-azaspiro[4.5]-decane.
155. 2-ethyl-2,5,8,8,10,10-hexamethyl-1,9-diazaspiro[5.5]undec-4-yl benzoate.
156. 2,2,6,6-tetramethyl-3-propyl-4-piperidyl benzoate.
157. 3-allyl-2,2,6,6-tetramethyl-4-piperidinol.
158. 3-allyl-2,2,6,6-tetramethyl-4-piperidyl benzoate.
159. bis(2,6-diethyl-2,3,6-trimethyl-4-piperidyl) carbonate.
160. bis(2,6-diethyl-2,3,6-trimethyl-4-piperidyl) oxalate.
161. bis(2,6-diethyl-2,3,6-trimethyl-4-piperidyl) succinate.
162. bis(2,6-diethyl-2,3,6-trimethyl-4-piperidyl) adipate.
163. bis(2,6-diethyl-2,3,6-trimethyl-4-piperidyl) sebacate.
164. bis(2,6-diethyl-2,3,6-trimethyl-4-piperidyl) 3,3'-thiodipropionate.
165. bis(2,6-diethyl-2,3,6-trimethyl-4-piperidyl) fumarate.
166. bis(2,6-diethyl-2,3,6-trimethyl-4-piperidyl) terephthalate.
167. bis(2,6-diethyl-2,3,6-trimethyl-4-piperidyl) isophthalate.
168. bis(2,6-diethyl-2,3,6-trimethyl-4-piperidyl) cyclohexane-1,4-dicarboxylate.
169. bis(2,6-diethyl-2,3,6-trimethyl-4-piperidyl) sulphite.
170. bis(2,6-diethyl-2,3,6-trimethyl-4-piperidyl) phenylphosphonate.
171. bis(2,6-diethyl-1,2,3,6-tetramethyl-4-piperidyl)succinate.
172. bis(2,6-diethyl-1,2,3,6-tetramethyl-4-piperidyl)adipate.
173. bis(2,6-diethyl-1,2,3,6-tetramethyl-4-piperidyl)sebacate.
174. bis(2,6-diethyl-1,2,3,6-tetramethyl-4-piperidyl)isophthalate.
175. bis[1-(2,3-epoxypropyl)-2,6-diethyl-2,3,6-trimethyl-4-piperidyl]isophthalate.
176. bis(1-benzyl-2,6-diethyl-2,3,6-trimethyl-4-piperidyl)sebacate.
177. bis[1-(2-acetoxyethyl)-2,6-diethyl-2,3,6-trimethyl-4-piperidyl]sebacate.
178. bis(2,6-diethyl-2,3,6-trimethyl-4-piperidyl) hexamethylenedicarbamate.
179. bis(2,6-diethyl-2,3,6-trimethyl-4-piperidyl) toluene-2,4-dicarbamate.
180. bis(2,6-diethyl-2,3,6-trimethyl-4-piperidyl) naphthalene-1,5-dicarbamate.
181. bis(2,6-diethyl-2,3,6-trimethyl-4-piperidyl) (p-phenylenedimethylene)dicarbamate.
182. bis(2,6-diethyl-2,3,6-trimethyl-4-piperidyl) (m-phenylenedimethylene)dicarbamate.
183. bis(2,6-diethyl-2,3,6-trimethyl-4-piperidyl) (oxydi-p-phenylene)dicarbamate.
184. bis(2,6-diethyl-2,3,6-trimethyl-4-piperidyl) (methylenedi-p-phenylene)dicarbamate.
185. bis(2,6-diethyl-2,3,6-trimethyl-4-piperidyl) 3,3'-dimethylbiphenyl-4,4'-dicarbamate.

186. bis(2,6-diethyl-2,3,6-trimethyl-4-piperidyl) (1,3-cyclohexylenedimethylene)dicarbamate.
187. bis(2,6-diethyl-2,3,6-trimethyl-4-piperidyl) (methylenedi-4,1-cyclohexylene)dicarbamate.
188. bis(2,6-diethyl-1,2,3,6-tetramethyl-4-piperidyl)hexamethylenedicarbamate.
189. bis(2,6-diethyl-1,2,3,6-tetramethyl-4-piperidyl)toluene-2,4-dicarbamate.
190. bis(2,6-diethyl-1,2,3,6-tetramethyl-4-piperidyl)(m-phenylenedimethylene)dicarbamate.
191. bis(2,6-diethyl-1,2,3,6-tetramethyl-4-piperidyl) (methylenedi-p-phenylene)dicarbamate.
192. bis(1-allyl-2,6-diethyl-2,3,6-trimethyl-4-piperidyl) (methylenedi-4,1-cyclohexylene)dicarbamate.
193. bis(1-benzyl-2,6-diethyl-2,3,6-trimethyl-4-piperidyl)toluene-2,4-dicarbamate.
194. bis[2,6-diethyl-2,3,6-trimethyl-1-(2-octanoyloxyethyl)-4-piperidyl] (m-phenylenedimethylene)dicarbamate.
195. 1,2-bis(2,6-diethyl-2,3,6-trimethyl-4-piperidyloxy)ethane.
196. 1,6-bis(2,6-diethyl-2,3,6-trimethyl-4-piperidyloxy)hexane.
197. 1,4-bis(2,6-diethyl-2,3,6-trimethyl-4-piperidyloxy)-but-2-ene.
198. 1,4-bis[(2,6-diethyl-2,3,6-trimethyl-4-piperidyloxy)methyl]benzene.
199. 1,3-bis[(2,6-diethyl-2,3,6-trimethyl-4-piperidyloxy)methyl]benzene.
200. 1,3-bis[(2,6-diethyl-1,2,3,6-tetramethyl-4-piperidyloxy)methyl]benzene.
201. 1,4-bis[(2,6-diethyl-1,2,3,6-tetramethyl-4-piperidyloxy)methyl]benzene.
202. 1,6-bis[2,6-diethyl-2,3,6-trimethyl-1-(2-stearoyloxyethyl)-4-piperidyloxy]hexane.
203. bis(3-isobutyl-2,6-diisopentyl-2,6-dimethyl-4-piperidyl)sebacate.
204. bis(3-isobutyl-2,6-diisopentyl-2,6-dimethyl-4-piperidyl)hexamethylenedicarbamate.
205. bis(2-ethyl-2,5-dimethyl-1-azaspiro[5.5]undec-4-yl)sebacate.
206. bis[6-(2-benzoyloxyethyl)-7-ethyl-7,10-dimethyl-6-azaspiro[4.5]dec-9-yl]succinate.
207. bis(3-allyl-2,2,6,6-tetramethyl-4-piperidyl) sebacate.
208. tris(2,6-diethyl-2,3,6-trimethyl-4-piperidyl) trimellitate.
209. tris(2,6-diethyl-2,3,6-trimethyl-4-piperidyl) trimesate.
210. tris(2,6-diethyl-2,3,6-trimethyl-4-piperidyl) phosphite.
211. tris(2,6-diethyl-2,3,6-trimethyl-4-piperidyl) phosphate.
212. 2,4,6-tris(2,6-diethyl-2,3,6-trimethyl-4-piperidyloxy)1,3,5-triazine.
213. 2,4,6-tris(2,6-diethyl-1,2,3,6-tetramethyl-4-piperidyloxy)-1,3,5-triazine.
214. tris(2,6-diethyl-1,2,3,6-tetramethyl-4-piperidyloxy)trimellitate.
215. tris(2,6-diethyl-1,2,3,6-tetramethyl-4-piperidyl)phosphite.
216. tris(1-benzyl-2,6-diethyl-2,3,6-trimethyl-4-piperidyl)phosphite.
217. tetrakis(2,6-diethyl-2,3,6-trimethyl-4-piperidyl)pyromellitate.
218. tetrakis(2,6-diethyl-1,2,3,6-tetramethyl-4-piperidyl)pyromellitate.
219. 2,6-diethyl-2,3,6-trimethyl-4-piperidyl 4-hydroxy-3,5-di-t-butylbenzoate.
220. 2,6-diethyl-2,3,6-trimethyl-4-piperidyl phenoxyacetate.
221. bis(2,6-diethyl-2,3,6-trimethyl-4-piperidyl)thiophene-2,5-dicarboxylate.
222. bis(2,6-diethyl-2,3,6-trimethyl-4-piperidyl)decane-1,10-dicarboxylate.
223. 4-(2,5-dioxa-1-phospholan-1-yloxy)-2,6-diethyl-2,3,6-trimethylpiperidine.
224. 4-(4,4-dimethyl-2,6-dioxa-1-phosphan-1-yloxy)-2,6-diethyl-2,3,6-trimethylpiperidine.
225. O-ethyl O'-(2,6-diethyl-2,3,6-trimethyl-4-piperidyl)benzylphosphonate.
226. O,O'-bis(2,6-diethyl-2,3,6-trimethyl-4-piperidyl)-phosphonate.
227. O,O'-bis(2,6-diethyl-2,3,6-trimethyl-4-piperidyl)-benzylphosphonate.
228. O,O'-bis(2,6-diethyl-2,3,6-trimethyl-4-piperidyl)4-hydroxy-3,5-di-t-butylbenzylphosphonate.
229. 3,9-bis(2,6-diethyl-2,3,6-trimethyl-4-piperidyloxy)-2,4,8,10-tetraoxa-3,9-diphosphaspiro[5.5]undecane.
230. 2,6-diethyl-4-hydroxy-2,3,6-trimethyl piperidine-1-oxyl.
231. methyl 3-(1-allyl-2,6-diethyl-2,3,6-trimethyl-4-piperidyloxy)crotonate.
232. tris(2,6-diethyl-2,3,6-trimethyl-4-piperidylborate.
233. 2-ethyl-2,5-dimethyl-1-azaspiro[5.5]undec-4-yl methyl adipate.
234. 3-ethyl-2,6-dimethyl-2,6-dipropyl-4-piperidinol.
235. 3-ethyl-2,6-dimethyl-2,6-dipropyl-4-piperidyl p-t-butylbenzoate.
236. 4,4'-bis(2,6-diethyl-2,3,6-trimethylpiperidin-4-yloxymethyl)diphenyl.

Of the above compounds, compounds 1 and 10 are disclosed in Berichte 41, 777 (1908) but it is not disclosed that these compounds have any use as polymer stabilizers.

The 4-piperidinol derivatives (I) may be prepared by any of the following methods, which can be carried out under known conditions:

Method A

Compounds of formula (I) wherein Y represents a hydrogen atom can be prepared by reducing a compound of formula (II):

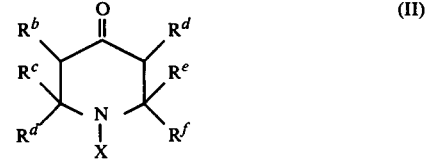

(wherein $R^a$, $R^b$, $R^c$, $R^d$, $R^e$, $R^f$ and X are as defined above, provided that X does not represent an oxyl radical) with a reducing agent such as sodium borohydride or with hydrogen and a catalyst such as Raney nickel.

Method B

Compounds of formula (I) wherein Y represents an acyl group, a group obtained by removing a hydroxy group from a sulphur-or phosphorus- containing acid, a diacyl group, a carbonyl group, a sulphinyl group, a sulphonyl group, a group obtained by removing two hydroxy groups from a phosphorus-containing acid, the group the group

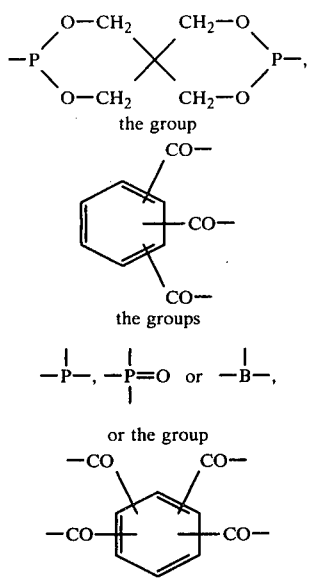

the groups $-\overset{|}{P}-$, $-\overset{|}{\underset{|}{P}}=O$ or $-\overset{|}{B}-$, or the group

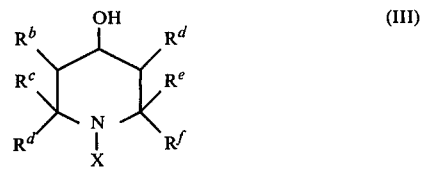

can be prepared by reacting a compound of formula (III)

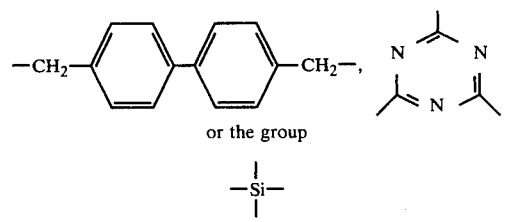

(wherein $R^a$, $R^b$, $R^c$, $R^d$, $R^e$, $R^f$ and X are as defined above) with a reactive derivative of the acid corresponding to the group Y, for example an acid halide or a lower alkyl ester.

Method C

Compounds of formula (I) wherein Y represents an alkyl group, an alkenyl group, an aralkyl group, a cyclohexyl group, an alkylene group, an alkenylene group, a xylylene group, the group

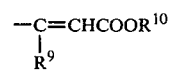

or the group $-\overset{|}{\underset{|}{Si}}-$ can be prepared by reacting a compound of formula (III), defined above, with a halide of the group Y.

Method D

Compounds of formula (I) wherein Y represents one of the groups —CO.NHR⁸ or —CO.NH.R¹².NH.CO— can be prepared by reacting a compound of the formula (III), defined above, with an isocyanate of formula R⁸NCO or OCN.R¹².NCO (wherein R⁸ and R¹² are as defined above).

Method E

Compounds of formula (I) wherein Y represents one of the groups

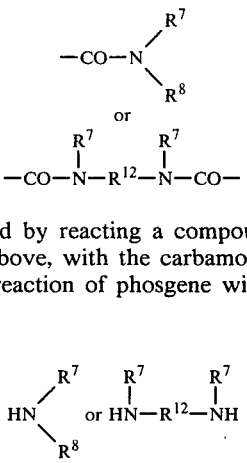

can be prepared by reacting a compound of formula (III), defined above, with the carbamoyl chloride obtained by the reaction of phosgene with an amine of formula $HN\overset{R^7}{\underset{R^8}{\diagdown}}$ or $HN\overset{R^7}{\underset{|}{-}}R^{12}\overset{R^7}{\underset{|}{-}}NH$ respectively ($R^7$, $R^8$ and $R^{12}$ being as defined above).

Method F

Compounds of formula (I) wherein Y represents the group —CO.R⁵.COOH can be prepared by reacting a compound of formula (III), defined above, with an acid anhydride of formula

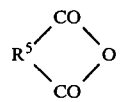

(wherein R⁵ is as defined above). Esters and salts of this group can readily be prepared by conventional methods. Alternatively, compounds wherein Y represents the lower alkyl ester of the group —CO.R⁵.COOH can be prepared by reacting a compound of formula (III), defined above, with an lower alkyl ester of the dicarboxylic acid corresponding to the group Y, preferably in approximately equimolar amounts.

Method G

Compounds of formula (I) wherein Y represents the group $-\underset{R^9}{\overset{|}{C}}=CHCOOR^{10}$ can be prepared by reacting a compound of formula (III), defined above, with a compound of formula R⁹.C≡C.COOR¹⁰ (wherein R⁹ and R¹⁰ are as defined above).

Where X represents a group other than a hydrogen atom, this group can be introduced into the compound simultaneously with, before or after the introduction of the substituent Y by treating the compound of formula (I), (II) or (III) wherein X represents a hydrogen atom by, for example, the following methods:

Method H

Compounds of formula (I), (II) or (III) wherein X represents an oxyl radical can be prepared by reacting the corresponding compound wherein X represents a hydrogen atom with a peroxide, such as hydrogen peroxide.

Method J

Compounds of formula (I), (II) or (III) wherein X represents an alkyl group, an alkenyl group, an alkoxyalkyl group, an aralkyl group, a 2,3-epoxypropyl group, the group —CH$_2$COOR$^1$, the group

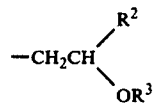

an aliphatic acyl group or the group —COOR$^4$ (R$^1$, R$^2$, R$^3$ and R$^4$ being as defined above) can be prepared by reacting the corresponding compound where X represents a hydrogen atom with a halide of the group X.

Method K

Compounds of formula (I), (II) or (III) wherein X represents the group

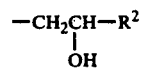

(R$^2$ being as defined above) can be prepared by reacting the corresponding compound wherein X represents a hydrogen atom with an epoxide, such as ethylene oxide, propylene oxide or styrene oxide. The compounds thus obtained may be acylated to give the corresponding acylated compounds.

Method L

Compounds of formula (I), (II) or (III) wherein X represents a methyl group can most advantageously be prepared by the Leuckart-Wallach reaction in which a corresponding compound wherein X represents a hydrogen atom is reacted with formic acid and formaldehyde.

Method M

Compounds of formula (I), (II) or (III) wherein X represents a formyl group can be prepared by reacting a corresponding compound wherein X represents a hydrogen atom with ethyl orthoformate in the presence of an acid catalyst.

Compounds of formula (II), which form the starting materials for producing the 4-piperidinol derivatives (I) used in the polymeric composition of the present invention can be prepared by a known series of reactions, e.g. as shown in the following reaction scheme (in this scheme, the symbols R$^g$, R$^k$, R$^e$ and R$^f$ are as previously defined):

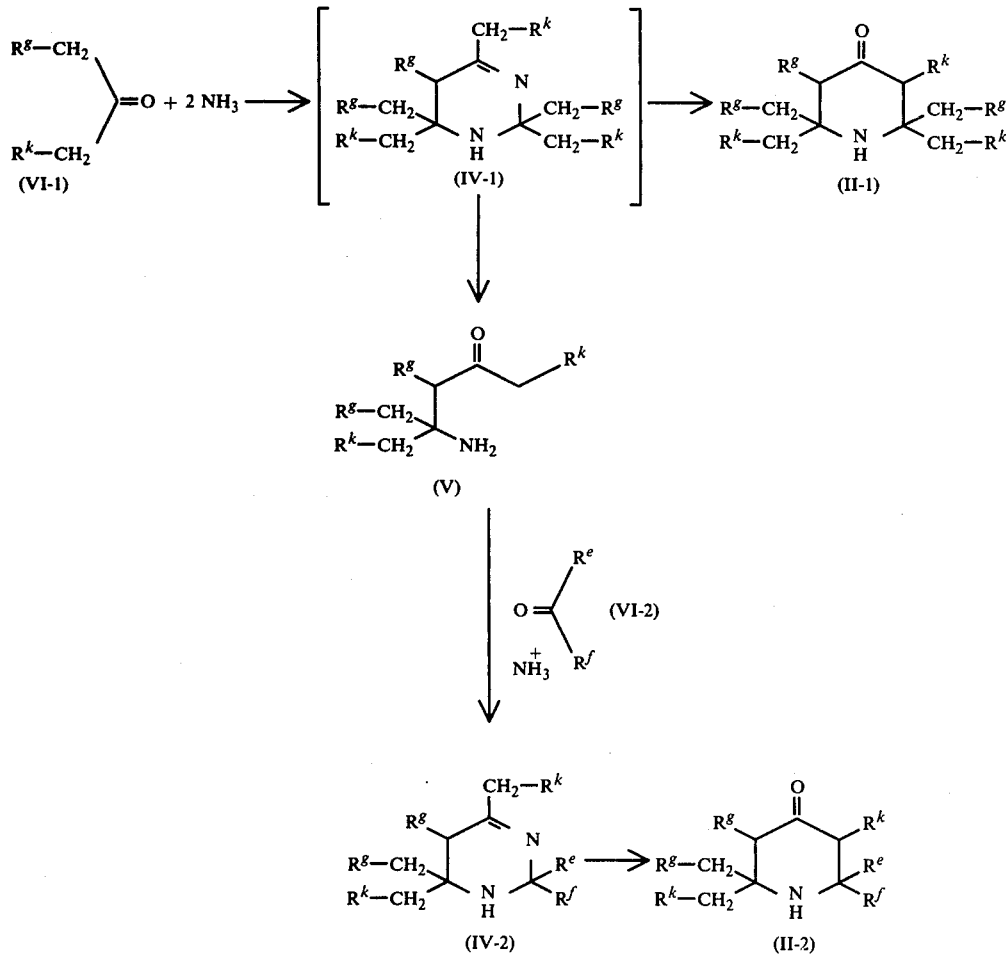

4-Piperidone derivatives of formula (II-1) may be prepared directly by contacting a ketone of formula (VI-1) for a long time with ammonia in an alcohol according to the method described in Berichte 41, 777 (1908).

Alternatively, the 4-piperidone derivative (II) may be prepared via a tetrahydropyrimidine derivative of formula (IV-1) which, in turn, is prepared by the reaction of the ketone (VI-1) with ammonia in the presence of an ammonium halide catalyst by the method described in U.S. Pat. No. 2,516,626. Most advantageous is a modification of this process, in which the reaction is carried out in the additional presence of a promoter selected from the group consisting of bromine, iodine, iodine trichloride, alkali metal iodides, hydroiodides of aliphatic amines having from 1 to 12 carbon atoms, lithium or ammonium rhodanide, lithium cyanide, ammonium sulphide, carboxylic acids, sulphonic acids, ammonium salts of carboxylic or sulphonic acids, or salts of nitrogen-containing organic bases with carboxylic or sulphonic acids, the promoters being used in an amount of from 0.01 to 0.5 mole % based on the amount of ketone. This method is described in more detail, as applied to the production of acetonin [a tetrahydropyrimidine derivative having a formula similar to (IV-1) except that $R^g$ and $R^k$ each represents a hydrogen atom] in U.S. application Ser. No. 515,815 filed Oct. 18, 1974.

Starting from the tetrahydropyrimidine derivative (IV-1) thus obtained, 4-piperidone derivatives of formula (II-1) may be prepared by methods similar to those known for the preparation of triacetonamine (2,2,6,6-tetramethyl-4-piperidone) from acetonine (2,2,4,4,6-pentamethyl-2,3,4,5-tetrahydropyrimidine), e.g. the following Methods A' to E':

Method A'

According to the method described in U.S. Pat. No. 3,513,170, 4-piperidone derivatives (II-1) may be prepared by reacting the corresponding tetrahydropyrimidine derivative (IV-1) with at least an equimolar amount (based on the tetrahydropyrimidine derivative) of water in the presence of more that 0.2 mole %, preferably more than 2 mole %, of a Lewis acid catalyst, such as calcium chloride, zinc chloride, aluminium chloride or boron trifluoride, especially calcium chloride. Yields of the desired compound may be greatly improved by carrying out the reaction using a ketone of formula (VI-1) as solvent and even better results are achieved by using a mixture of this ketone with methanol. The reaction is advantageously carried out at temperatures ranging from room temperature to the reflux temperature of the solvent employed.

Method B'

Following the procedure described in U.S. application Ser. No. 481,838 filed June 21, 1974, 4-piperidone derivatives (II-1) may be prepared by reacting the corresponding tetrahydropyrimidine derivative (IV-1) with water in the presence of a catalyst which is: a mineral acid, e.g. hydrochloric acid; a carboxylic acid; an organic sulphur oxyacid, e.g. p-toluenesulphonic acid; an organic phosphorus oxyacid; or an ammonium or nitrogen-containing organic base salt of one of these acids, e.g. ammonium chloride or ammonium bromide. The catalyst is suitably used in an amount of at least 12.5 mole % based on the amount of tetrahydropyrimidine derivative.

Method C'

Following the procedure described in U.S. application Ser. No. 481,839 filed June 21, 1974, 4-piperidone derivatives of formula (II-1) may be prepared by reacting the corresponding tetrahydropyrimidine derivative (IV-1) with a ketone of formula (VI-1) under anhydrous conditions in the presence of an acid catalyst, preferably employed in an amount of at least 12.5 mole % based on the tetrahydropyrimidine derivative.

Method D'

Following the procedure described in U.S. application Ser. No. 481,921 filed June 21, 1974, 4-piperidone derivatives of formula (II-1) may be prepared by treating the corresponding tetrahydropyrimidine derivative (IV-1) with a ketone of formula (VI-1) in the presence of an acid catalyst (suitably in an amount of from 0.2 to 12 mole % based on the tetrahydropyrimidine derivative) and in the presence or absence of water.

Method E'

Following the procedure described in U.S. application Ser. No. 481,935 filed June 21, 1974, a process similar to that of method D' may be carried out in the absence of catalyst.

Method F'

Following the procedure described in U.S. application Ser. No. 481,922 filed June 21, 1974, 4-piperidone derivatives of formula (II-1) may be prepared by reacting the ketone (VI-1) with ammonia at a temperature of from 5° to 60° C. in the presence of from 0.2 to 12 mole % (based on the ketone) of an acid catalyst and then, after (if necessary) adding further ketone so that the ratio of total ketone in the reaction system to ammonia is 1.6:1 or more, further heating the reaction mixture to complete the reaction.

Examples of 4-piperidone derivatives of formula (II-1) which may be prepared by the above methods and which may be employed as starting materials to prepare the 4-piperidinol derivatives used in the present invention are as follows:

2,6-diethyl-2,3,6-trimethyl-4-piperidone bp 91°–93° C./2.0 mmHg.

3=ethyl-2,6-dimethyl-2,6-dipropyl-4-piperidone bp 115°–118° C./1.5 mmHg.

2,6-diisobutyl-3-isopropyl-2,6-dimethyl-4-piperidone bp 129°–131° C./2.0 mmHg.

3-isobutyl-2,6-diisopentyl-2,6-dimethyl-4-piperidone. bp 144°–146° C./0.2 mmHg.

2,2,6,6-tetraethyl-3,5-dimethyl-4-piperidone mp 77°–78° C.

Alternatively, instead of proceeding via 4-piperidone derivatives (II-1), the tetrahydropyrmidine derivative of formula (IV-1) may be converted, as shown in the foregoing reaction scheme, to an aminoketone derivative of formula (V) by testing it with an aqueous solution of a strong acid (e.g. hydrochloric or sulphuric acid) according to the method described in Helv. Chim. Acta 30, 1114 (1947) and then reacting the aminoketone derivative (V) thus obtained with a ketone of formula (VI-2) and ammonia to give a 1,2,5,6-tetrahydropyrimidine derivative of formula (IV-2) having different substituents at the 2- and 6- positions using the method described in Monatsh. Chem. 88, 464 (1957). The resulting tetrahydropyrimidine derivative of formula (IV-2) may then be reacted by any of the methods described above in connection with tetrahydropyrimidine derivative (IV-1) to give a 4-piperidone derivative of formula (II-2) having differing substituents at the 2- and 6- positions.

As a still further alternative, a 2,2,6,6-tetrasubstituted-4-piperidone derivative which is unsubstituted at the 3- and/or 5- positions may be reacted with a secondary amine (such as piperidine or morpholine) to give a corresponding enamine derivative, which is then reacted with a halogenated hydrocarbon (such as allyl bromide); the reaction product thus obtained is hydrolized to give a compound having a hydrocarbon group at the 3- or 5- position by the method of J. Szmuszkovicz [Adv. Org. Chem. 4, 2 (1963)]. If desired, if the hydrocarbon radical introduced at the 3- or 5- position is unsaturated, it may be reduced by conventional methods to give the corresponding saturated hydrocarbon radical.

The 4-piperidinol derivatives of general formula (I) are useful for stabilizing polymers, especially synthetic polymers, against photo- and/or thermal- deterioration.

Organic polymers which can be stabilized in this way include:

olefin and diene polymers including homopolymers of olefins and dienes (e.g. low-density, high-density and cross-linked polyethylenes, polypropylene, polyisobutylene, polymethylbutene-1, polymethylpentene-1, polyisoprene and polybutadiene), mixtures of such homopolymers (e.g. mixtures of polypropylene and polyethylene, polypropylene and polybutene-1, or polypropylene or polyisobutylene), and copolymers of olefins and dienes (e.g. ethylene/propylene copolymers, propylene/butene-1 copolymers, propylene/isobutylene copolymers, ethylene/butene-1 copolymers, and terpolymers of ethylene and propylene with dienes such as hexadiene, dicyclopentadiene or ethylidene norbornene);

styrene polymers including polystyrene, copolymers of styrene and of α-methylstyrene (e.g. styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength), and graft copolymers of styrene (e.g. polymers in which styrene is grafted onto polybutadiene, and polymers in which styrene and acrylonitrile are grafted onto polybutadiene as well as mixtures thereof with the aforementioned styrene copolymer commonly known as acrylonitrile/butadiene/styrene of ABS plastics);

halogenated vinyl and vinylidene polymers including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids and derivatives thereof, including polyacrylates and polymethacrylates, polyacrylic amides and polyacrylonitrile;

polymers derived from unsaturated alcohols and amines and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers (e.g. ethylene/vinyl acetate copolymers);

epoxy polymers including homopolymers and copolymers derived from epoxides (e.g. polyethylene oxide), and polymers derived from bis-glycidyl ethers;

polyacetals, polyalkylene oxides and polyphenylene oxides including polyoxymethylene, oxymethylene/ethylene oxide copolymers, polyoxyethylene, polypropylene oxide, polyisobutylene oxide and polyphenylene oxides;

polyurethanes and polyureas;

polycarbonates;

polysulphones;

polyamides and copolyamides derived from diamines and dicarboxylic acids and/or from aminocarboxylic acids or the corresponding lactams, including nylon-6, nylon-6,6 nylon-6,10, nylon-11 and nylon-12;

polyesters derived from dicarboxylic acids and dialcohols and/or from hydroxycarboxylic acids and the corresponding lactones, e.g. polyethylene glycol terephthalate and poly-1,4-dimethylol-cyclohexane terephthalate;

cross-linked polymers derived from aldehydes together with phenols, ureas or melamines, e.g. phenol/formaldehyde, urea/formaldehyde and melamine/formaldehyde resins;

alkyd resins e.g. glycerol/phthalic acid resins and mixtures thereof with melamine/formaldehyde resins;

unsaturated polyester resins derived from copolyesters of saturated and unsaturated dicarboxylic acids with polyhydric alcohols as well as from vinyl compounds as cross-linking agents, and also halogenated flame-resistant modifications thereof; and natural polymers including cellulose, rubber and proteins, as well as chemically modified homologues thereof (e.g. cellulose acetates, cellulose propionates, cellulose butyrates and cellulose ethers such as methyl cellulose).

The amount of the stabilizers of the invention needed for effective stabilization of organic polymers will depend on a variety of factors, such as the type and properties of the polymer concerned, its intended use, and the presence of other stabilizers. It is generally satisfactory to use from 0.01% to 5% by weight of the stabilizers of the invention, based on the weight of the polymer, but the most effective range will vary with the type of polymer; viz. 0.01% to 2.0%, preferably 0.02% to 1.0%, by weight for olefin, diene and styrene polymers; 0.01% to 1.0%, preferably 0.02% to 0.5%, by weight for vinyl and vinylidene polymers; and 0.01% to 5.0%, preferably 0.02% to 2.0%, by weight for polyurethanes and polyamides. If desired, two or more of the stabilizers of the invention may be used together.

The 4-piperidinol derivatives of formula (I), employed as stabilizers in the polymeric compositions of the invention, may readily be incorporated into the polymers to be stabilized by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer.

The stabilized polymeric compositions of the present invention may optionally also contain various conventional additives, such as the following:

Antioxidants

Simple, 2,6-dialkylphenols, such as, for example, 2,6-di-t-butyl-4-methylphenol, 2-t-butyl-4,6-dimethylphenol, 2,6-di-t-butyl-4-methoxymethylphenol and 2,6-dioctadecyl-4-methylphenol.

Derivatives of alkylated hydroquinones, such as, for example, 2,5-di-t-butylhydroquinone, 2,5-di-t-amylhydroquinone, 2,6-di-t-butylhydroquinone, 2,5-di-t-butyl-4-hydroxyanisole, 3,5-di-t-butyl-4-hydroxyanisole, tris(3,5-di-t-butyl-4-hydroxyphenyl)phosphite, 3,5-di-t-butyl-4-hydroxyphenylstearate and di-(3,5-di-t-butyl-4-hydroxyphenyl)adipate.

Hydroxylated thiodiphenyl ethers, such as, for example, 2,2'-thiobis(6-t-butyl-4-methylphenol), 2,2'-thiobis(4-octylphenol), 4,4'-thiobis(6-t-butyl-3-methylphenol), 4,4'-thiobis(3,6-di-s-amylphenol), 4,4'-thiobis(6-t-butyl-2-methylphenol) and 4,4'-bis(2,6-dimethyl-4-hydroxyphenyl)disulphide.

Alkylidene-bisphenols, such as, for example, 2,2'-methylene-bis(6-t-butyl-4-methylphenol), 2,2'-methylene-bis(6-t-butyl-4-ethylphenol), 4,4'-methylene-bis(6-t-butyl-2-methylphenol), 4,4'-methylene-bis(2,6-di-t-butylphenol), 2,6-di-(3-t-butyl-5-methyl-2-hydroxybenzyl)-4-methylphenol, 2,2'-methylene-bis[4-methyl-6-(α-methylcyclohexyl)phenol], 1,1-bis(3,5-dimethyl-2-hydroxyphenyl)butane, 1,1-bis(5-t-butyl-4-hydroxy-2-methylphenyl)butane, 2,2-bis(5-t-butyl-4-hydroxy-2-methylphenyl)butane, 2,2-bis(3,5-di-t-butyl-4-hydroxyphenyl)propane, 1,1,3-tris(5-t-butyl-4-hydroxy-2-methylphenyl)butane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane and ethylene glycol bis[3,3-bis(3'-t-butyl-4'-hydroxyphenyl)butyrate].

O-, N- and S-benzyl compounds, such as, for example, 3,5,3',5'-tetra-t-butyl-4,4'-dihydroxydibenzyl ether, 4-hydroxy-3,5-dimethylbenzyl-mercaptoacetic acid octadecyl ester, tri(3,5-di-t-butyl-4-hydroxybenzyl)amine, and bis(4-t-butyl-3-hydroxy-2,6-dimethylbenzyl)dithiolterephthalate.

Hydroxybenzylated malonic esters, such as, for example, 2,2-bis(3,5-di-t-butyl-2-hydroxybenzyl)malonic acid dioctadecyl ester, 2-(3-t-butyl-4-hydroxy-5-methylbenzyl)malonic acid dioctadecyl ester, 2,2-bis(3,5-di-t-butyl-4-hydroxybenzyl)malonic acid didodecyl-mercaptoethyl ester, and 2,2-bis(3,5-di-t-butyl-4-hydroxybenzyl)malonic acid di(4-t-octylphenyl)ester.

Hydroxybenzyl aromatics, such as, for example, 1,3,5-tri(3,5-di-t-butyl-4-hydroxybenzyl)-2,4,6-trimethylbenzene, 1,4-di(3,5-di-t-butyl-4-hydroxybenzyl)-2,3,5,6-tetramethylbenzene, and 2,4,6-tri(3,5-di-t-butyl-4-hydroxybenzyl)phenol.

s-Triazine compounds, such as, for example, 2,4-bis-octylmercapto-6-(3,5-di-t-butyl-4-hydroxyanilino)-s-triazine, 2-octylmercapto-4,6-bis(3,5-di-t-butyl-4-hydroxyanilino)-s-triazine, 2-octylmercapto-4,6-bis(3,5-di-t-butyl-4-hydroxyphenoxy)-s-triazine, 2,4,6-tris(3,5-di-t-butyl-4-hydroxyphenoxy)-s-triazine, 2,4,6-tris(3,5-di-t-butyl-4-hydroxyphenylethyl)-s-triazine, and 1,3,5-tris(3,5-di-t-butyl-4-hydroxybenzyl)isocyanurate.

Amides of 3,5-di-t-butyl-4-hydroxyphenylpropionic acid, such as, for example, 1,3,5-tris(3,5-di-t-butyl-4-hydroxyphenyl-propionyl)hexahydro-s-triazine, and N,N'-bis(3,5-di-t-butyl-4-hydroxyphenylpropionyl)hexamethylenediamine.

Esters of 3,5-di-t-butyl-4-hydroxyphenylpropionic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethyl isocyanurate, and 4-hydroxymethyl-1-phospha-2,6,7-trioxabicyclo[2,2,2]octane.

Esters of 5-t-butyl-4-hydroxy-3-methylphenylpropionic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethyl isocyanurate, and 4-hydroxymethyl-1-phospha-2,6,7-trioxabicyclo[2,2,2]octane.

Esters of 3,5-di-t-butyl-4-hydroxyphenylacetic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethyl isocyanurate, and 4-hydroxymethyl-1-phospha-2,6,7-trioxabicyclo[2,2,2]octane.

Acylaminophenols, such as, for example, N-(3,5-di-t-butyl-4-hydroxyphenyl)stearic acid amide and N,N'-bis(3,5-di-t-butyl-4-hydroxyphenyl)thiobisacetamide.

Benzylphosphonates, such as, for example, 3,5-di-t-butyl-4-hydroxybenzylphosphonic acid dimethyl ester, 3,5-di-t-butyl-4-hydroxybenzylphosphonic acid diethyl ester, 3,5-di-t-butyl-4-hydroxybenzylphosphonic acid dioctadecyl ester, and 5-t-butyl-4-hydroxy-3-methylbenzylphosphonic acid dioctadecyl ester.

Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-s-butyl-p-phenylenediamine, 6-ethoxy-2,2,4-trimethyl-1,2-dihydroquinoline, 6-dodecyl-2,2,4-trimethyl-1,2-dihydroquinoline, mono- and di-octyliminodibenzyl, and polymerized 2,2,4-trimethyl-1,2-dihydroquinoline.

UV-absorbers and Light Protection Agents 2-(2'-Hydroxyphenyl)benztriazoles, such as, for example, the 5'-methyl, 3',5'-di-t-butyl, 5'-t-butyl, 5'-(1,1,3,3-tetramethylbutyl), 5-chloro-3',5'-di-t-butyl, 5-chloro-3'-t-butyl-5'-methyl, 3'-s-butyl-5'-t-butyl, 3'-[α-methylbenzyl]-5'-methyl, 3'-[α-methylbenzyl]-5'-methyl-5-chloro, 4'-hydroxy, 4'-methoxy, 4'-octoxy, 3',5'-di-t-amyl, 3'-methyl-5'-carbomethoxyethyl and 5-chloro-3',5'-di-t-amyl derivatives.

2,4-Bis(2'-hydroxyphenyl)-6-alkyl-s-triazines, such as, for example, the 6-ethyl, 6-undecyl and 6-heptadecyl derivatives.

2-Hydroxybenzophenones, such as, for example, the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

1,3-Bis(2'-hydroxybenzoyl)benzenes, such as, for example, 1,3-bis(2'-hydroxy-4'-hexyloxybenzoyl)benzene, 1,3-bis(2'-hydroxy-4'-octoxybenzoyl)benzene and 1,3-bis(2'-hydroxy-4'-dodecyloxybenzoyl)benzene.

Esters of optionally substituted benzoic acids, such as, for example, phenyl salicylate, octylphenyl salicylate, dibenzoylresorcinol, bis(4-t-butylbenzoyl)resorcinol, benzoylresorcinol and 3,5-di-t-butyl-4-hydroxybenzoic acid 2,4-di-t-butylphenyl ester, octadecyl ester or 2-methyl-4,6-di-t-butylphenyl ester.

Acrylates, such as, for example, α-cyano-β,β-diphenylacrylic acid ethyl ester or iso-octyl ester, α-carbomethoxycinnamic acid methyl ester, α-cyano-β-methyl-p-methoxycinnamic acid methyl ester or butyl ester, and N-(β-carbomethoxyvinyl)-2-methylindoline.

Nickel compounds, for example, nickel complexes of 2,2'-thiobis(4-t-octylphenol), such as the 1:1 and 1:2 complexes, optionally with other ligands such as n-butylamine, triethanolamine or N-cyclohexyldiethanolamine; nickel complexes of bis(4-t-octylphenyl)-sulphone, such as the 2:1 complex, optionally with other ligands such as 2-ethylcaproic acid; nickel dibutyldithiocarbamate; nickel salts of 4-hydroxy-3,5-di-t-butylbenzylphosphonic acid monoalkyl esters, such as the methyl, ethyl or butyl ester; the nickel complex of 2-hydroxy-4-methylphenyl undecyl ketonoxime; and nickel 3,5-di-t-butyl-4-hydroxybenzoate.

Oxalic acid diamides, such as, for example, 4,4'-dioctyloxyoxanilide, 2,2'-dioctyloxy-5,5'-di-t-butyloxanilide, 2,2'-di-dodecyloxy-5,5'-di-t-butyloxanilide, 2-ethoxy-5-t-butyl-2'-ethyloxanilide, 2-ethoxy-2'-ethyloxanilide, N,N'-bis(3-dimethylaminopropyl)oxalamide, mixtures of o- and p-methoxy and o- and p-ethoxy-di-substituted oxanilides, and mixtures of 2-ethoxy-5-t-butyl-2'-ethyloxanilide with 2-ethoxy-2'-ethyl-5,4'-di-t-butyloxanilide.

Metal deactivators, such as, for example, oxanilide, isophthalic acid dihydrazide, sebacic acid bisphenylhydrazide, bisbenzylidene oxalic acid dihydrazide, N,N'-diacetyladipic acid dihydrazide, N,N'-bis-salicyloyloxalic acid dihydrazide, N,N'-bis-salicyloylhydrazine, and N,N'-bis(3,5-di-t-butyl-4-hydroxyphenylpropionyl)hydrazine.

Phosphites, such as, for example, triphenyl phosphite, diphenyl alkyl phosphites, phenyl dialkyl phosphites, trinonyl phenyl phosphite, trilauryl phosphite, trioctadecyl phosphite, 3,9-di-isodecyloxy-2,4,8,10-tetraoxa-3,9-diphosphaspiro[5,5]undecane, and tris(4-hydroxy-3,5-di-t-butylphenyl)phosphite.

Peroxide deactivators, such as, for example, esters of β-thiodipropionic acid (e.g., the lauryl, stearyl, myristyl and tridecyl esters), salts of 2-mercaptobenzimidazole (e.g., the zinc salt), and diphenylthiourea.

Polyamide stabilizers, such as, for example, copper salts in combination with iodides and/or phosphorus compounds and salts of divalent manganese.

Basic co-stabilizers, such as, for example, polyvinylpyrrolidone, melamine, benzoguanamine, triallyl cyanurate, dicyandiamide, urea derivatives, hydrazine derivatives, amines, polyamides, polyurethanes, and alkali metal salts and alkaline earth metal salts of higher saturated or unsaturated fatty acids, (e.g., Ca stearate, Mg laurate, Na ricinoleate, K palmitate and Zn stearate).

PVC stabilizers, such as, for example, organic tin compounds, organic lead compounds and Ba/Cd salts of fatty acids.

Nucleating agents, such as, for example, 4-t-butylbenzoic acid, adipic acid, and diphenylacetic acid.

Other additives, such as, for example, plasticizers, lubricants (e.g., glycerol monostearate), emulsifiers, antistatic agents, flameproofing agents, pigments, carbon black, asbestos, glass fibre, kaolin and talc.

The use of the stabilizers of formula (I) with the above-listed antioxidants is particularly effective for the stabilization of olefin polymers.

The invention is further illustrated by the following Preparations and Example, in which all parts and percentages are by weight. Preparations A to D illustrate the preparation of 4-piperidone starting materials, whilst Preparations 1 to 10 illustrate the preparation of the 4-piperidinol derivatives of formula (I). The Example illustrates the stabilization of various synthetic polymers using the 4-piperidinol derivatives of formula (I), which are identified by the numbers appended to them in the list given hereinbefore.

PREPARATION A 2,6-diethyl-2,3,6-trimethyl-4-piperidone

To an ice-cooled mixture of 39.2 g of 2,4,6-triethyl-2,6-dimethyl-1,2,5,6-tetrahydropyrimidine and 18.0 g of methyl ethyl ketone were added 14.7 g of powdered calcium chloride dihydrate, followed by 3 ml of water. The resulting mixture was heated at 60° C., with stirring, for 15 hours, made alkaline by the addition of a 35% aqueous solution of sodium hydroxide and extracted with diethyl ether. The ethereal solution was then dried over potassium carbonate and the diethyl ether was evaporated off. The residue was distilled under reduced pressure, giving 32.4 g of the title compound. Boiling point 91°–93° C./2.0 mmHg.

PREPARATION B 2,6-diethyl-2,3,6-trimethyl-4-piperidone 19.6 g of 2,4,6-triethyl-2,6-dimethyl-1,2,5,6-tetrahydropyrimidine and 0.4 g of ammonium bromide were added to 200 ml of methanol. To the mixture were added dropwise 10 g of a 37% aqueous hydrochloric acid solution at 10° C., with stirring. When the addition was complete, the whole mixture was stirred at room temperature for 4 hours, after which 20 ml of 18% aqueous hydrochloric acid were then added. The mixture was then heated at 30°–40° C. for 7 hours and allowed to stand overnight at room temperature. The resulting mixture was made alkaline by addition of a 40% aqueous solution of potassium carbonate and, after evaporating off the methanol under reduced pressure, the mixture was extracted with diethyl ether. The ethereal extract was dried over potassium carbonate, after which the diethyl ether was removed. The residue was then distilled under reduced pressure, giving 15.1 g of the title compound as an oil boiling at 91°–93° C./2.0 mmHg.

PREPARATION C 2-ethyl-2,5-dimethyl-1-azaspiro[5.5]undecan-4-one 196.3 g of 2,4,6-triethyl-2,6-dimethyl-1,2,5,6-tetrahydropyrimidine were added dropwise to 300 ml of concentrated hydrochloric acid at 30°–40° C., with stirring. When all of the tetrahydropyrimidine had been added, the entire mixture was stirred for 4–5 hours and then neutralized with sodium carbonate and extracted with benzene. The resulting benzene solution was washed, in turn, with a 5% aqueous solution of sodium carbonate and with water, and was then dried over potassium carbonate. After removing the benzene, the residue was distilled under reduced pressure, giving 72.4 g of 5- amino-5-methyl-3-heptanone (bp 46°–48° C./2.5 mmHg).

14.3 g of the 5-amino-5-methyl-3-heptanone thus obtained were dissolved in 100 ml of methanol, and 10.0 g of cyclohexanone and 10.0 g of ammonium bromide were added to the resulting solution. Dry ammonia was then introduced into the solution at room temperature for a period of 6 hours. After allowing the solution to stand overnight, 10.0 g of potassium carbonate were added and the methanol was then removed by distillation under reduced pressure. The residue was extracted with benzene, washed with water and dried over potassium carbonate. The benzene was then removed and the residue was distilled under reduced pressure, giving 14.0 g of 2,4-diethyl-4-methyl-1,5-diazaspiro[5.5]undec-1-ene (bp 93°–94° C./1.5 mmHg).

11.1 g of the 2,4-diethyl-4-methyl-1,5-diazaspiro[5.5]undec-1-ene thus obtained and 2.5 g of ammonium bromide were dissolved in 70 ml of methanol. 45 ml of water were added to the solution, with stirring. The mixture was then stirred at room temperature for 8 hours. Methanol was removed by evaporation under reduced pressure and the residue was then distilled under reduced pressure, giving 7.4 g of the title product, bp 119°–122° C./1.5 mmHg.

PREPARATION D

3-allyl-2,2,6,6-tetramethyl-4-piperidone 154.7 g of 2,2,6,6-tetramethyl-4-piperidone, 160 g of piperidine and 10.0 g of p-toluenesulphonic acid monohydrate were dissolved in 200 ml of benzene. The solution was refluxed by heating for 8.5 hours, whilst the water formed in situ was removed with a Dean-Stark separator. The reaction mixture was then poured into a mixture comprising 700 ml of water, 200 ml of concentrated aqueous ammonia and 100 g of ice. The organic layer was separated, washed three times with water and then dried over anhydrous magnesium sulphate. After removing the solvent, the residue was distilled under reduced pressure, giving 46.6 g of 1,2,5,6-tetrahydro-2,2,6,6-tetramethyl-4-piperidinopyridine (bp 80°–82° C./1 mmHg).

2.2 g of the 1,2,5,6-tetrahydro-2,2,6,6-tetramethyl-4-piperidinopyridine thus obtained and 1.2 g of allyl bromide were dissolved in 3 ml of chloroform and the solution was allowed to stand for 24 hours at room temperature. The crystals which precipitated were filtered off, washed with hexane and dissolved in 4 ml of concentrated aqueous ammonia; the solution was then extracted with hexane. extract was dried over potassium carbonate and, after removing the hexane, 1.3 g of 5-allyl-1,2,5,6-tetrahydro-2,2,6,6-tetramethyl-4-piperidinopyridine were obtained. The compound showed a single spot on thin layer chromatography using a 0.25 mm thick layer of alumina (available from Merck & Co. under the trade name "60F 254") and using a mixture of benzene/hexane/ethyl acetate/triethylamine (2:2:1:0.5 by volume) as developing solvent; the $R_f$ value was 0.80.

1.46 g of the 5-allyl-1,2,5,6-tetrahydro-2,2,6,6-tetramethyl-4-piperidinopyridine thus obtained were dissolved in a mixture of 3 ml of acetic acid, 1.5 g of sodium acetate and 3 ml of water, and the solution was allowed to stand overnight. To the solution were then added 6.0 g of sodium bicarbonate and 3 ml of concentrated aqueous ammonia; the mixture was then extracted with hexane. The extract was dried over anhydrous magnesium sulphate and then treated with charcoal. 0.91 g of the title compound was obtained after removal of the hexane. The compound showed a single spot on thin layer chromatography using a 0.25 mm thick layer of alumina and a mixture of benzene/hexane/ethyl acetate/triethylamine (2:2:1:0.5 by volume) as developing solvent; $R_f$ value 0.70.

PREPARATION 1

2,6-diethyl-2,3,6-trimethyl-4-piperidinol (Compound 1)

19.7 g of 2,6-diethyl-2,3,6-trimethyl-4-piperidone were dissolved in 250 ml of methanol, and 3.7 g of sodium borohydride were added thereto in four portions over a period of 1 hour, with stirring. After stirring the mixture for a further 4 hours, it was allowed to stand overnight and was then concentrated by evaporation under reduced pressure; water was added to the concentrated mixture, which was then extracted with benzene. The resulting benzene solution was dried over potassium carbonate and the benzene was distilled off. The residue was distilled under reduced pressure, giving 17.2 g of the title compound as a colourless liquid (bp 125°–129° C./1.5 mmHg).

PREPARATION 2

2,6-diethyl-2,3,6-trimethyl-4-piperidyl p-t-butylbenzoate (Compound 11)

15.0 g of 2,6-diethyl-2,3,6-trimethyl-4-piperidinol (Compound 1) and 16.0 g of methyl p-t-butylbenzoate were dissolved in 500 ml of heptane. 1.5 g of lithium amide were then added to the solution and the mixture was refluxed by heating in a flask equipped with a Dean-Stark separator. 1.5 g of methanol were first removed and this was followed by 200 ml of heptane, which distilled off over a period of 3 hours. After cooling the reaction mixture, it was washed with water and dried over magnesium sulphate; the solvent was then removed by evaporation under reduced pressure. The residue was distilled under reduced pressure, giving 28.2 g of the title compound as a colourless liquid (bp 176°–178° C./0.008 mmHg).

The following acid addition salts of this compound were obtained by mixing a solution of Compound 11 with a solution of the appropriate acid and separating the resulting crystals of the salt:

p-toluenesulphonate: mp 91°–93° C.;
p-t-butylbenzoate: mp 129°–131° C.;
0.5 sulphate: mp 234°–243° C.

PREPARATION 3

Bis(2,6-diethyl-2,3,6-trimethyl-4-piperidyl)sulphite (Compound 169)

8.0 g of 2,6-diethyl-2,3,6-trimethyl-4-piperidinol (Compound 1) and 6.0 g of triethylamine were dissolved in 100 ml of benzene. 2.4 g of thionyl chloride in 30 ml of benzene were then added dropwise at 10°–15° C. When the addition was complete the mixture was stirred at 25°–30° C. for 1 hour and then filtered. The filtrate was washed with, in turn, an aqueous solution of sodium carbonate and water, and was then dried over anhydrous sodium sulphate. After removing the solvent, the residue was distilled under reduced pressure, giving 6.0 g of Compound 169 as a pale yellow oil (bp 180° C./0.008 mmHg).

PREPARATION 4

2,6-diethyl-2,3,6-trimethyl-4-piperidyl methylcarbamate (Compound 66)

4.0 g of 2,6-diethyl-2,3,6-trimethyl-4-piperidinol (Compound 1) and 1.7 g of methyl isocyanate were dissolved in 6 ml of xylene and the solution was refluxed by heating for 3.5 hours. Xylene and excess methyl isocyanate were distilled off under reduced pressure. The residue was purified by column chromatography on silica gel ("60F 254", available from Merck & Co.) using a 4 : 1 by volume mixture of chloroform and methanol as eluent. The product was then distilled under reduced pressure, giving 5.0 g of Compound 66 as a pale yellow liquid (bp 145°–149° C./1.4 mmHg).

The acid addition salt of this compound with formic acid was obtained by conventional means and found to have a melting point of 166° C.

PREPARATION 5

4-benzyloxy-2,6-diethyl-2,3,6-trimethylpiperidine (Compound 95)

To a solution of 3.0 g of 2,6-diethyl-2,3,6-trimethyl-4-piperidinol (Compound 1) in 30 ml of dry toluene was added, at 0°–5° C., 0.65 g of sodium hydride (purity 52.9%). The mixture was refluxed by heating for 6 hours. After cooling the mixture, 1.9 g of benzyl chloride were added dropwise at 0°–5° C. and the resulting mixture was refluxed by heating for 4 hours. The reaction mixture was then washed with water and dried over anhydrous magnesium sulphate; the solvent was then distilled off. The residue was purified by column chromatography on silica gel using benzene as eluent, followed by distillation under reduced pressure. There were obtained 2.1 g of Compound 95 as a pale yellow oil (bp 120°–124° C./0.2 mmHg).

PREPARATION 6

Methyl 3-(2,6-diethyl-2,3,6-trimethyl-4-piperidyloxy)crotonate (Compound 97)

To a solution of 3.0 g of 2,6-diethyl-2,3,6-trimethyl-4-piperidinol (Compound 1) in 30 ml of benzene was added, in small portions at room temperature, 0.72 g of 50% sodium hydride. The mixture was then stirred for 30 minutes at room temperature. A solution of 2.2 g of methyl tetrolate in 10 ml of benzene was then added dropwise, with ice-cooling, to the mixture and the whole mixture was stirred at room temperature for 64 hours. The mixture was then poured into ice water and extracted with ethyl acetate. The extract was washed with a saturated aqueous solution of sodium chloride and then dried over anhydrous sodium sulphate. After removing the solvent, the residue was distilled under reduced pressure, giving 3.4 g of Compound 97 as a pale yellow oil (bp 109°–111° C./0.15 mmHg).

PREPARATION 7

1-allyl-2,6-diethyl-2,3,6-trimethyl-4-piperidyl benzoate (Compound 36)

To a solution of 6.0 g of 2,6-diethyl-2,3,6-trimethyl-4-piperidyl benzoate (Compound 10 - prepared using the same procedure as is described in Preparation 2) in 20 ml of dimethylformamide were added 6.0 g of allyl bromide, and the mixture was heated at 110°–115° C. for 9 hours. The mixture was then concentrated by evaporation under reduced pressure and 50 ml of benzene were added. The resulting mixture was then washed, in turn, with an aqueous solution of sodium carbonate and with water and was then dried over anhydrous sodium sulphate. After removing the solvent, the residue was distilled under reduced pressure, giving 1.6 g of Compound 36 as a colourless, viscous liquid (bp 163° C./0.004 mmHg).

PREPARATION 8

4-benzyloxy-2,6-diethyl-1,2,3,6-tetramethylpiperidine (Compound 100)

To 1.0 g of 4-benzyloxy-2,6-diethyl-2,3,6-trimethylpiperidine (Compound 95 - prepared as described in Preparation 5) were added 0.52 g of formic acid and 1.22 g of 37% formalin at 0°–5° C. The mixture was stirred at room temperature and then refluxed by heating for 3 hours. When the reaction was complete, the reaction mixture was adjusted to a pH value of 8.0 by addition of a 5% aqueous solution of sodium bicarbonate; the mixture was then extracted with ethyl acetate. The extract was dried over anhydrous magnesium sulphate and the solvent was removed by evaporation under reduced pressure. The residue was purified by column chromatography on silica gel using benzene as eluent; the resulting product was then distilled under reduced pressure, giving 0.6 g of Compound 100 as a pale yellow liquid (bp 132°–135° C./0.2 mmHg).

PREPARATION 9

2,6-diethyl-1-(2-hydroxyethyl)-2,3,6-trimethyl-4-piperidyl methylcarbamate (Compound 84)

To a solution of 5.1 g of 2,6-diethyl-2,3,6-trimethyl-4-piperidyl methylcarbamate (Compound 66 - prepared as described in Preparation 4) in 8 ml of methanol were added 1.74 g of ethylene oxide and 1 drop of concentrated hydrochloric acid. The mixture was heated overnight at 100° C. in a sealed tube. When the reaction was complete, the reaction mixture was concentrated by evaporation under reduced pressure and the residue was purified by column chromatography on silica gel using a 1 : 1 by volume mixture of benzene and ethyl acetate as eluent, giving 3.0 g of Compound 84. The compound showed a single spot on thin layer chromatography on silica gel (developing solvent: benzene/ethyl acetate, 1 : 1 by volume), $R_f$ value 0.51.

PREPARATION 10

1-(2-acetoxyethyl)-2,6-diethyl-2,3,6-trimethyl-4-piperidyl benzoate (Compound 50)

To a solution of 2.5 g of 2,6-diethyl-1-(2-hydroxyethyl)-2,3,6-trimethyl-4-piperidyl benzoate (Compound 45 - prepared following the procedure described in Preparation 9) in 50 ml of dimethylformamide were added 2.0 g of triethylamine and 1 g of acetic anhydride; the mixture was then heated at 80°–90° C. for 5 hours. When the reaction was complete, the reaction mixture was concentrated and 50 ml of benzene were added. The mixture was then washed with, in turn, an aqueous solution of sodium carbonate and water, and was dried over anhydrous sodium sulphate. After removing the solvent, the residue was subjected to distillation under reduced pressure, giving 1.2 g of Compound 50 as a colourless oil (bp 195° C./0.0008 mmHg).

The following compounds were prepared by substantially the same methods as are described in Preparations 1 to 10.

2,6-diethyl-2,3,6-trimethyl-4-piperidyl acetate (Compound 2) bp 102° C./3 mmHg 2,6-diethyl-2,3,6-trimethyl-4-piperidyl stearate (Compound 5) bp 210°–213° C./0.1 mmHg 2,6-diethyl-2,3,6-trimethyl-4-piperidyl crotonate (Compound 7) bp 220°–230° C./0.1 mmHg 2,6-diethyl-2,3,6-trimethyl-4-piperidyl tetrolate (Compound 9) bp 110°–112° C./0.2 mmHg 2,6-diethyl-2,3,6-trimethyl-4-piperidyl benzoate (Compound 10) bp 161°–163° C./0.8 mmHg 2,6-diethyl-2,3,6-trimethyl-4-piperidyl β-(4-hydroxy-3,5-di-t-butylphenyl)propionate (Compound 17) bp 216°–218° C./0.005 mmHg p-t-butylbenzoate of 2,6-diethyl-2,3,6-trimethyl-4-piperidyl β-(4-hydroxy-3,5-di-t-butylphenyl)propionate mp 57°–59° C.

2,6-diethyl-1,2,3,6-tetramethyl-4-piperidyl benzoate (Compound 28) bp 152°–153° C./0.65 mmHg 2,6-diethyl-1,2,3,6-tetramethyl-4-piperidyl p-toluenesulfonate (Compound 32)

TLC: $R_f =$ 0.47 (silica gel; ethyl acetate:benzene = 1:5 by volume)

1-benzyl-2,6-diethyl-2,3,6-trimethyl-4-piperidyl acetate (Compound 37) bp 160° C./3 mmHg 1-(2,3-epoxypropyl)-2,6-diethyl-2,3,6-trimethyl-4-piperidyl benzoate (Compound 43) bp 195°–197° C./0.25 mmHg 2,6-diethyl-1-(2-hydroxyethyl)-2,3,6-trimethyl-4-piperidyl benzoate (Compound 45)

TLC: $R_f =$ 0.61 (silica gel; ethyl acetate:benzene = 1:1 by volume)

1-(2-benzoyloxyethyl)-2,6-diethyl-2,3,6-trimethyl-4-piperidyl benzoate (Compound 54) bp 195°–197° C./0.45 mmHg 1-acetyl-2,6-diethyl-2,3,6-trimethyl-4-piperidyl benzoate (Compound 64) bp 185°–187° C./0.45 mmHg 2,6-diethyl-2,3,6-trimethyl-4-piperidyl ethyl carbamate (Compound 67) bp 155° C./1.3 mmHg 2,6-diethyl-2,3,6-trimethyl-4-piperidyl octadecylcarbamate (Compound 68) mp 45°–47° C.

2,6-diethyl-2,3,6-trimethyl-4-piperidyl carbanilate (Compound 69)

TLC: $R_f =$ 0.50 (alumina; ethyl acetate:benzene = 1:2 by volume)

formate of 2,6-diethyl-2,3,6-trimethyl-4-piperidyl carbanilate mp 155°–167° C.

2,6-diethyl-2,3,6-trimethyl-4-piperidyl p-chlorocarbanilate (Compound 71) mp 168°–175° C. (as formate)

2,6-diethyl-2,3,6-trimethyl-4-piperydyl 1-naphthalenecarbamate (Compound 72) mp 82°–90° C.

2,6-diethyl-2,3,6-trimethyl-4-piperidyl cyclohexanecarbamate (Compound 73) mp 57°–64° C.

2,6-diethyl-1,2,3,6-tetramethyl-4-piperidyl methylcarbamate (Compound 77 as monohydrate)

TLC: $R_f =$ 0.58 (silica gel; ethyl acetate:benzene = 1:1 by volume)

1-allyl-2,6-diethyl-2,3,6-trimethyl-4-piperidyl methylcarbamate (Compound 80)

TLC: $R_f =$ 0.53 (silica gel; ethyl acetate:benzene = 1:9 by volume)

1-benzyl-2,6-diethyl-2,3,6-trimethyl-4-piperidyl methylcarbamate (Compound 81) mp 100°–103° C.

1-benzyl-2,6-diethyl-2,3,6-trimethyl-4-piperidyl N-benzyl-N-methylcarbamate (Compound 82)

TLC: $R_f =$ 0.61 (silica gel; ethyl acetate:benzene = 1:9 by volume)

1-benzyl-2,6-diethyl-2,3,6-trimethyl-4-piperidyl cyclohexanecarbamate (Compound 83) mp 152°–155° C.

1-(2-acetoxyethyl)-2,6-diethyl-2,3,6-trimethyl-4-piperidyl methylcarbamate (Compound 85)

TLC: $R_f =$ 0.44 (silica gel; ethyl acetate:benzene = 1:9 by volume)

2,6-diethyl-4-methoxy-2,3,6-trimethylpiperidine (Compound 91) bp 90°–94° C./0.3 mmHg 2,6-diethyl-2,3,6-trimethyl-4-octadecyloxypiperidine (Compound 93) bp 205°–210° C./0.2 mmHg ethyl β-(2,6-diethyl-2,3,6-trimethyl-4-piperidyloxy)acrylate (Compound 96) bp 138°–140° C./0.002 mmHg 1-allyl-2,6-diethyl-2,3,6-trimethyl-4-octadecyloxypiperidine (Compound 101)

TLC: $R_f =$ 0.49 (silica gel; benzene:ethyl acetate = 30:1 by volume)

1-benzyl-2,6-diethyl-4-methoxy-2,3,6-trimethylpiperidine (Compound 103) bp 115°–118° C./0.15 mmHg 2,6-diethyl-1-(2-hydroxyethyl)-4-methoxy-2,3,6-trimethylpiperidine (Compound 104) bp 118°–120° C./0.15 mmHg 1-(2-acetoxyethyl)-2,6-diethyl-4-methoxy-2,3,6-trimethylpiperidine (Compound 105) bp 116°–119° C./0.15 mmHg 2,2,6,6-tetraethyl-3,5-dimethyl-4-piperidinol (Compound 107) bp 134°–136° C./2.5 mmHg 2,2,6,6-tetraethyl-3,5-dimethyl-4-piperidyl hexanoate (Compound 108) bp 146°–148° C./0.5 mmHg 2,2,6,6-tetraethyl-3,5-dimethyl-4-piperidyl benzoate (Compound 109) bp 161°–164° C./0.4 mmHg 2,2,6,6-tetraethyl-3,5-dimethyl-4-piperidyl m-nitrobenzoate (Compound 110) bp 185°–188° C./0.3 mmHg 3-isobutyl-2,6-diisopentyl-2,6-dimethyl-4-piperidinol (Compound 125) bp 132°–134° C./1.5 mmHg 3-isobutyl-2,6-diisopentyl-2,6-dimethyl-4-piperidyl benzoate (Compound 126) bp 181°–183° C./1.0 mmHg 6-ethyl-2,3,6-trimethyl-2-nonyl-4-piperidinol (Compound 132) bp 148°–153° C./0.1 mmHg 6-ethyl-2,3,6-trimethyl-2-nonyl-4-piperidyl p-t-butylbenzoate (Compound 133) bp 218°–222° C./0.005 mmHg 6-ethyl-2,3,6-trimethyl-2-phenethyl-4-piperidinol (Compound 135) bp 148°–149° C./1.0 mmHg 6-ethyl-2,3,6-trimethyl-2-phenethyl-4-piperidyl valerate (Compound 136) bp 176°–179° C./1.0 mmHg 6-ethyl-2,3,6-trimethyl-2-phenethyl-4-piperidyl p-t-butylbenzoate (Compound 137) bp 184°–186° C./0.08 mmHg 6-ethyl-2,3,6-trimethyl-2-(3-pyridyl)-4-piperidinol (Compound 144) bp 165°–168° C./1 mmHg 6-ethyl-2,3,6-trimethyl-2-(3-pyridyl)-4-piperidyl benzoate (Compound 145) bp 210°–213° C./1 mmHg 2-ethyl-2,5-dimethyl-1-azaspiro[5.5]undecan-4-ol (Compound 147) bp 125°–129° C./1.5 mmHg 2-ethyl-2,5-dimethyl-1-azaspiro[5.5]undec-4-yl benzoate (Compound 149) bp 189°–190° C./1.0 mmHg 2-ethyl-2,5-dimethyl-1-azaspiro[5.5]undec-4-yl methylcarbamate (Compound 150) bp 156°–158° C./0.007 mmHg 4-benzyloxy-2-ethyl-2,5-dimethyl-1-azaspiro[5.5]undecane (Compound 151) bp 161°–162° C./0.003 mmHg 2,2,6,6-tetramethyl-3-propyl-4-piperidyl benzoate (Compound 156)

TLC: $R_f =$ 0.40 (alumina; hexane:benzene:ethyl acetate = 2:2:1 by volume)

3-allyl-2,2,6,6-tetramethyl-4-piperidinol (Compound 157)

TLC: $R_f$ = 0.20 (alumina; hexane:ether = 1:1 by volume)

3-allyl-2,2,6,6-tetramethyl-4-piperidyl benzoate (Compound 158)

TLC: $R_f$ = 0.40 (alumina; benzene:hexane:ethyl acetate = 2:2:1 by volume)

bis(2,6-diethyl-2,3,6-trimethyl-4-piperidyl) carbonate (Compound 159)

TLC: $R_f$ = 0.60 (alumina; ethyl acetate:benzene = 1:4 by volume)

bis(2,6-diethyl-2,3,6-trimethyl-4-piperidyl) succinate (Compound 161) bp 184° C./0.02 mmHg bis(2,6-diethyl-2,3,6-trimethyl-4-piperidyl) sebacate (Compound 163) bp 268°-272° C./0.3 mmHg di(p-t-butylbenzoate) of bis(2,6-diethyl-2,3,6-trimethyl-4-piperidyl) sebacate mp 54°-56° C.

bis(2,6-diethyl-2,3,6-trimethyl-4-piperidyl) terephthalate (Compound 166) bp 237°-239° C./0.003 mmHg bis(2,6-diethyl-2,3,6-trimethyl-4-piperidyl) hexamethylenedicarbamate (Compound 178) mp 105°-115° C. (as diformate)

bis(2,6-diethyl-2,3,6-trimethyl-4-piperidyl) toluene-2,4-dicarbamate (Compound 179)

TLC: $R_f$ = 0.41 (alumina; ethyl acetate:methanol = 1:1 by volume)

bis(2,6-diethyl-2,3,6-trimethyl-4-piperidyl) (methylene-di-p-phenylene)dicarbamate (Compound 184)

TLC: $R_f$ = 0.42 (alumina; ethyl acetate:methanol = 1:1 by volume)

1,4-bis[(2,6-diethyl-2,3,6-trimethyl-4-piperidyloxy)methyl]benzene (Compound 198) bp 198°-201° C./0.15 mmHg tris(2,6-diethyl-2,3,6-trimethyl-4-piperidyl)trimesate (Compound 209)

TLC: $R_f$ = 0.59 (alumina; ethyl acetate:benzene = 1:1 by volume)

tris(2,6-diethyl-2,3,6-trimethyl-4-piperidyl)phosphite (Compound 210)

TLC: $R_f$ = 0.61 (alumina; ethyl acetate:benzene = 1:1 by volume)

2,6-diethyl-4-hydroxy-2,3,6-trimethylpiperidine-1-oxyl (Compound 230) mp 86°-87° C.

methyl 3-(1-allyl-2,6-diethyl-2,3,6-trimethyl-4-piperidyloxy)crotonate (Compound 231) bp 130°-135° C./0.1 mmHg 2-ethyl-2,5-dimethyl-1-azaspiro[5.5]undec-4-yl methyl adipate (Compound 233) bp 181°-182° C./0.05 mmHg 3-ethyl-2,6-dimethyl-2,6-dipropyl-4-piperidinol (Compound 234) bp 159°-160° C./2.5 mmHg 3-ethyl-2,6-dimethyl-2,6-dipropyl-4-piperidyl p-t-butylbenzoate (Compound 235) bp 224°-225° C./0.005 mmHg In the above, the abbreviation "TLC" stands for "Thin Layer chromatography".

EXAMPLE

Mixtures were made from 100 parts of unstabilized polypropylene (MFI about 20) and 0.25 part of each in turn of the stabilizers shown in the following Table. The resulting mixtures were blended, melted and moulded under heat and pressure into films of thickness 0.1 mm. Control sheets were also made, one of the controls containing no stabilizer and the other containing Tinuvin 327, a Trade Mark for 2-(2-hydroxy-3,5-di-t-butylphenyl)-5-chlorobenzo-1,2,3-triazole, sold by Ciba-Geigy AG.

The sheets thus formed were exposed to ultraviolet radiation at 45° C. in the "Standard Fade-Meter Type FA-1", manufactured and sold by Toyo Rika Instruments, Japan, a modification of the Atlas Fade-O-Meter Type FDA-R, which meets the requirements of paragraph 3.8 of Japanese Industrial Standard 1044-L.

The time taken before the sheets became brittle was measured and the results were expressed as a ratio of the time required for the sheet to become brittle when a stabilizer was used to the time required for the sheet to become brittle in the absence of stabilizer. The results are shown in the following Table.

Table

| Stabilizer Compound No. | | Ratio |
|---|---|---|
| 1 | | 12.5 |
| 2 | | 15 |
| 5 | | 24.5 |
| 7 | | 31 |
| 9 | | 18.5 |
| 10 | | 18.5 |
| 11 | | 14 |
| 11 | (p-t-butylbenzoate) | 20.5 |
| 11 | (0.5 sulphate) | 20 |
| 17 | | 15.5 |
| 17 | p-t-butylbenzoate) | 13 |
| 28 | | 15 |
| 36 | | 15 |
| 37 | | 14.5 |
| 43 | | 24.5 |
| 50 | | 23 |
| 54 | | 39 |
| 64 | | 18.5 |
| 67 | | 10 |
| 68 | | 16.5 |
| 69 | | 15.5 |
| 72 | | 10 |
| 73 | | 15.5 |
| 77 | (as monohydrate) | 21.5 |
| 80 | | 24.5 |
| 81 | | 16 |
| 82 | | 27 |
| 83 | | 24.5 |
| 84 | | 18 |
| 85 | | 18.5 |
| 91 | | 12.5 |
| 93 | | 21 |
| 95 | | 11.5 |
| 96 | | 16 |
| 100 | | 17 |
| 101 | | 38 |
| 103 | | 17 |
| 105 | | 13.5 |
| 107 | | 8.5 |
| 108 | | 12 |
| 109 | | 9 |
| 110 | | 10.5 |
| 125 | | 17.5 |
| 126 | | 18 |
| 133 | | 16 |
| 135 | | 15 |
| 136 | | 14 |
| 137 | | 15 |
| 145 | | 18 |
| 149 | | 21 |
| 150 | | 18.5 |
| 151 | | 18 |
| 159 | | 35.5 |
| 163 | | 19.5 |
| 163 | (di-p-t-butylbenzoate) | 11.5 |
| 166 | | 14.5 |
| 169 | | 14.5 |
| 178 | (di-formate) | 29 |
| 179 | | 15 |
| 184 | | 13.5 |
| 198 | | 17 |
| 209 | | 38.5 |
| 210 | | 38 |
| 231 | | 22.5 |
| 235 | | 15 |
| None | (control) | 1 |
| Tinuvin 327 | (control) | 6.5 |

What is claimed is:

1. A polymer composition stabilized against photo- and thermal- deterioration wherein there is incorporated, in an amount sufficient to prevent said deterioration, a stabilizer comprising a 4-piperidinol derivative having the formula (I)

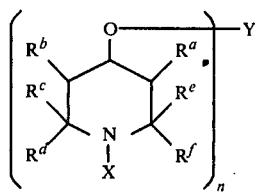
(I)

or an acid addition salt thereof, wherein:

$R^1$ and $R^b$ are the same or different and each represents a hydrogen atom, a lower alkyl group, an alkenyl group, an alkynyl group or an aralkyl group, provided that $R^a$ and $R^b$ do not simultaneously represent hydrogen atoms;

$R^c$ and $R^d$ are the same or different and each represents a lower alkyl group;

$R^e$ represents an alkyl group;

$R^f$ represents an alkyl group, a phenyl group, an aralkyl group or a 5- or 6-membered aromatic heterocyclic group containing an oxygen, sulphur or nitrogen atom; or $R^e$ and $R^f$, together with the carbon atom to which they are attached, represent a cycloalkyl group or a group of the formula

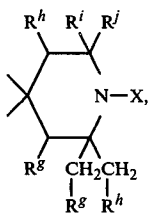

wherein $R^g$ and $R^h$ are the same or different and each represents a hydrogen atom or a lower alkyl group, provided that $R^h$ does not represent a hydrogen atom when $R^g$ represents a lower alkyl group; $R^i$ and $R^j$ are the same or different and each represents a lower alkyl group; and X is as hereafter defined:

X represents a hydrogen atom, an oxyl radical, an alkyl group, an alkenyl group, an alkoxy-alkyl group, an aralkyl group, which is unsubstituted or which has one or more substituents in its aryl moiety, a 2,3-epoxypropyl group, a group of formula —CH$_2$COOR$^1$ wherein R$^1$ represents an alkyl group, an alkenyl group, a phenyl group, an aralkyl group or a cyclohexyl group; a group of formula:

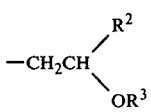

wherein $R^2$ represents a hydrogen atom, a methyl group or a phenyl group and $R^3$ represents a hydrogen atom or an acyl group; an aliphatic acyl group or a group of formula —COOR$^4$ wherein R$^4$ represents an alkyl group, a benzyl group or a phenyl group;

n is an integer of from 1 to 4 inclusive;

when n = 1:

Y represents: a hydrogen atom; an aliphatic, araliphatic, alicyclic, aromatic or heterocyclic acyl group;

a group of formula —CO.R$^5$.COOH wherein R$^5$ represents an alkylene group, whose chain may optionally be interrupted by a sulphur atom, or a phenylene group, or a metal salt or a lower alkyl ester thereof;

a monovalent group obtained by removing a hydroxy group from a sulphur-containing acid;

a monovalent group obtained by removing a hydroxy group from a phosphorus-containing acid;

a group of formula

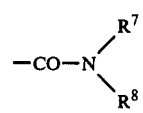

wherein $R^7$ represents a hydrogen atom, a lower alkyl group, an aralkyl group or a phenyl group; and $R^8$ represents an alkyl group, a substituted or unsubstituted aryl group, an aralkyl group or a cyclohexyl group; or $R^7$ and $R^8$, together with the nitrogen atom to which they are attached, represent a piperidino group, a 1-pyrrolidinyl group or a morpholino group;

an alkyl group;

an alkenyl group;

an aralkyl group, which is unsubstituted or has one or more substituents in its aryl moiety;

a cyclohexyl group; or a group having the formula:

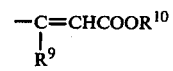

in which $R^9$ represents a hydrogen atom, a methyl group or a phenyl group and $R^{10}$ represents an alkyl group;

when n = 2:

Y represents an aliphatic, araliphatic, aromatic, alicyclic or heterocyclic diacyl group;

a carbonyl group;

a sulphinyl group;

a sulphonyl group;

a group obtained by removing two hydroxy groups from a phosphorus-containing acid;

a group of formula

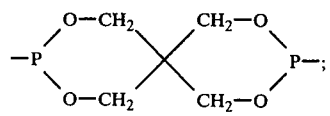

a group of formula

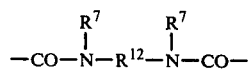

in which $R^7$ is as defined above and $R^{12}$ represents an alkylene group, an arylene group, which is unsubstituted or has one or more methyl substituents, a xylylene group, a cyclohexylene group, a group of formula

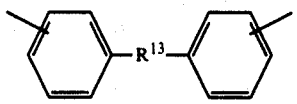

(in which $R^{13}$ represents an oxygen atom or a methylene group); a group of formula

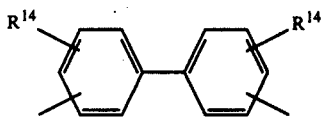

(in which $R^{14}$ represents a hydrogen atom or a methyl group); a group of formula

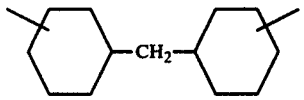

or a group of formula

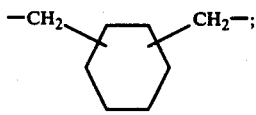

an alkylene group;
an alkenylene group;
a xylylene group or a group of the formula

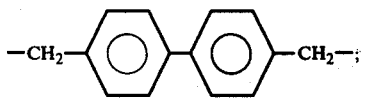

when n = 3:

Y represents: a group having the formula

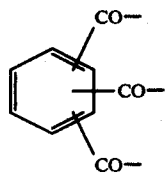

a group of formula

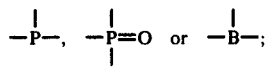

or a group of the formula

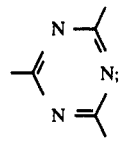

when n = 4:

Y represents: a group of the formula

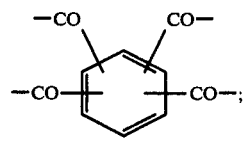

or a group of the formula

2. A polymer composition according to claim 1, wherein said 4-piperidinol derivative is incorporated in an amount of from 0.01 to 5.0% by weight, based upon the weight of the polymer.

3. A polymer composition according to claim 1, wherein said polymer is an olefin or diene polymer.

4. A polymer composition according to claim 1, wherein said polymer is a halogenated vinyl or vinylidene polymer.

5. A polymer composition according to claim 1, wherein said polymer is a polyurethane.

6. A polymer composition according to claim 1, wherein said polymer is a polyamide.

7. A polymer composition according to claim 1, wherein Y is as defined but other than hydrogen.

8. A polymer composition according to claim 1, wherein $R^a$ and $R^b$ are the same or different and each represents a hydrogen atom, an alkyl group having from 1 to 4 carbon atoms, an alkenyl group having 3 or 4 carbon atoms, or an alkynyl group having 3 or 4 carbon atoms, a benzyl group or a phenylethyl group, provided that $R^a$ and $R^b$ do not simultaneously represent a hydrogen atom;

$R^c$ and $R^d$ are the same or different and each represents an alkyl group having from 1 to 5 carbon atoms;

$R^e$ represents an alkyl group having from 1 to 9 carbon atoms;

$R^f$ represents an alkyl group having from 1 to 9 carbon atoms, a phenyl group, a benzyl or phenylethyl group, a 2-, 3- or 4-pyridyl, 2-furyl or 2-thienyl group, or $R^e$ and $R^f$, together with the carbon atom to which they are attached, represent a cycloalkyl group having from 5 to 7 carbon atoms, a 2,2,6,6-tetramethylpiperidyl group or a 2,6-diethyl-2,3,6-trimethylpiperidyl group;

X represents a hydrogen atom; an oxyl group; an alkyl group having from 1 to 8 carbon atoms; an alkenyl group having from 3 to 6 carbon atoms; an alkoxyalkyl group having from 1 to 3 carbon atoms in its alkyl moiety and from 1 to 18 carbon atoms in its alkoxy moiety;

an aralkyl group having 7 or 8 carbon atoms, which is unsubstituted or has up to 3 chlorine, $C_{1-4}$ alkyl, $C_{1-8}$ alkoxy or hydroxy substituents, the substituents being the same or different;

a 2,3-epoxypropyl group;

a group of the formula —$CH_2$—$COOR^1$ wherein
  $R^1$ is an alkyl group having from 1 to 18 carbon atoms,
  an alkenyl group having from 3 to 6 carbon atoms,
  a phenyl group, a benzyl group, a phenethyl group or a cyclohexyl group;

a group of the formula

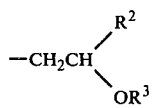

wherein
  $R^2$ represents a hydrogen atom, a methyl group of a phenyl group, and
  $R^3$ represents a hydrogen atom or a group of the formula —$COR^{15}$ in which
    $R^{15}$ represents an alkyl group having from 1 to 17 carbon atoms, an alkenyl group having from 2 to 4 carbon atoms, a phenyl group which is unsubstituted or has up to 3 chlorine, $C_{1-4}$ alkyl, $C_{1-8}$ alkoxy or hydroxy substituents, the substituents being the same or different, an aralkyl group having 7 or 8 carbon atoms which is unsubstituted or has up to 3 chlorine, $C_{1-4}$ alkyl, $C_{1-8}$ alkoxy or hydroxy substituents in its aryl moiety, the substituents being the same or different, a styryl group or a cyclohexyl group;

an alkanoyl or alkenoyl group having up to 4 carbon atoms; or a group of the formula —$COOR^4$ in which
  $R^4$ represents an alkyl group having from 1 to 8 carbon atoms, a benzyl group or a phenyl group;

when n = 1:

Y represents a hydrogen atom; a group of the formula —$COR^{16}$ in which
  $R^{16}$ represents a hydrogen atom, an alkyl group having from 1 to 17 carbon atoms, an alkenyl group having from 2 to 5 carbon atoms,
  an alkynyl group having 2 or 3 carbon atoms,
  a phenyl group which is unsubstituted or has up to 3 chlorine, $C_{1-4}$ alkyl, $C_{1-8}$ alkoxy, hydroxy or nitro substituents, the substituents being the same or different,
  a naphthyl group,
  a styryl group,
  an aralkyl group having 7 or 8 carbon atoms which may be unsubstituted or have up to 3 chlorine, $C_{1-4}$ alkyl, $C_{1-8}$ alkoxy or hydroxy substituents, the substituents being the same or different,
  a phenoxymethyl group,
  a cyclohexyl group,
  a 2-, 3- or 4-pyridyl group,
  a 2-furyl group or
  a 2-thienyl group;
a group of the formula —CO—$R^5$—COOH in which $R^5$ represents an alkylene group having from 1 to 10 carbon atoms whose chain may be interrupted by a sulfur atom; or a phenylene group;

or a metal salt thereof or an alkyl ester thereof having from 1 to 4 carbon atoms in its alkyl moiety;

a group of the formula —$SO_2.R^6$ in which
  $R^6$ represents an alkyl group having from 1 to 3 carbon atoms, a phenyl group or a tolyl group;

a group of the formula

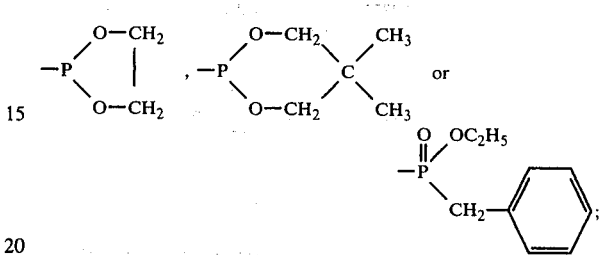

a group of the formula

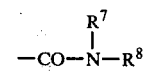

in which
  $R^7$ represents a hydrogen atom, an alkyl group having from 1 to 4 carbon atoms,
  a benzyl group a phenylethyl group or
  a phenyl group, and
  $R^8$ represents an alkyl group having from 1 to 18 carbon atoms, a phenyl group which may be unsubstituted or substituted by a chlorine atom or an alkyl group having from 1 to 4 carbon atoms,
  a naphthyl group, a benzyl group, a phenylethyl group or a cyclohexyl group, or
  $R^7$ and $R^8$ together with the nitrogen atom to which they are attached, represent
  a piperidino group,
  a 1-pyrrolidinyl group or a morpholino group;

an alkyl group having from 1 to 18 carbon atoms;
an alkenyl group having from 3 to 6 carbon atoms;
an aralkyl group having from 7 to 9 carbon atoms which is unsubstituted or substituted with up to 3 $C_{1-4}$ alkyl and/or hydroxy substituents in its aryl moiety;
a cyclohexyl group; or
a group of the formula

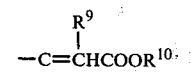

in which
  $R^9$ represents a hydrogen atom, a methyl group or a phenyl group, and
  $R^{10}$ represents an alkyl group having from 1 to 8 carbon atoms;

when n = 2:

Y represents a group of the formula —CO—($R^{17}$)$_m$—CO— in which
  m is 0 or 1; and $R^{17}$ represents an alkylene group having from 1 to 10 carbon atoms, the chain of which may be interrupted by a sulfur atom,
an alkenylene group having from 2 to 4 carbon atoms,
a phenylene group,
a cyclohexylene group,
a 2,4-pyridinediyl group,
a 2,5-pyridinediyl group, or
a 2,5-thiophenediyl group;
a carbonyl group;
a sulphinyl group;
a sulfonyl group;
a group of the formula $$\diagdown P - R^{11} \quad \text{or} \quad \diagdown \overset{\overset{O}{\|}}{P} - R^{11}$$

in which
$R^{11}$ represents a hydrogen atom, an alkyl group having from 1 to 4 carbon atoms,
a phenyl group, a benzyl group, or a 4-hydroxy-3,5-di-tert-butylbenzyl group;
a group of the formula $$-P \diagup \overset{O-CH_2}{\underset{O-CH_2}{\diagdown}} \diagdown \overset{CH_2-O}{\underset{CH_2-O}{\diagup}} P-;$$

a group of the formula $$-CO-\overset{R^7}{\underset{N}{|}}-R^{12}-\overset{R^7}{\underset{N}{|}}-CO-$$

in which
$R^7$ is as defined above; and
$R^{12}$ represents an alkylene group having from 2 to 10 carbon atoms, an arylene group having from 6 to 10 carbon atoms and optionally having one or more methyl substituents, a cyclohexylene group, a group of the formula

[structure: two phenyl rings connected by $R^{13}$]

in which
$R^{13}$ represents an oxygen atom or a methylene group,
a group of the formula

[structure: biphenyl with $R^{14}$ substituents]

in which
$R^{14}$ represents a hydrogen atom or a methyl group,
a group of the formula

[structure: two cyclohexyl rings connected by CH$_2$]  or

[structure: $-CH_2-$cyclohexyl$-CH_2-$];

an alkylene group having from 1 to 10 carbon atoms;
an alkenylene group having from 4 to 10 carbon atoms;
a xylylene group; or
a group of the formula

[structure: $-CH_2-$biphenyl$-CH_2-$];

when n = 4:
Y represents a group of the formula

[structure: benzene with four $-CO-$ groups at 1,2,4,5 positions];

or a group of the formula $$-\overset{|}{\underset{|}{Si}}-.$$

9. A polymer composition according to claim 8, wherein Y is as defined but other than hydrogen.

10. A polymer composition according to claim 1, wherein $R^a$ and $R^b$ are the same or different and each represents a hydrogen atom, an alkyl group having from 1 to 4 carbon atoms, or an allyl group, provided that $R^a$ and $R^b$ do not simultaneously represent a hydrogen atom;
$R^c$ and $R^d$ are the same or different and each represents an alkyl group having from 1 to 5 carbon atoms;
$R^e$ represents an alkyl group having from 1 to 5 carbon atoms;
$R^f$ represents an alkyl group having from 1 to 9 carbon atoms, a phenyl group, a benzyl or 2-phenylethyl group, a 2-, 3- or 4-pyridyl group or a 2-furyl group, or
$R^e$ and $R^f$, together with the carbon atom to which they are attached, represent a cyclopentyl group, a cyclohexyl group or a 2,2,6,6-tetramethylpiperidyl group;
X represents a hydrogen atom;
an alkyl group having from 1 to 8 carbon atoms;
an alkenyl group having 3 or 4 carbon atoms;
an alkoxyalkyl group having in all from 3 to 6 carbon atoms;
a benzyl group;
a methylbenzyl group;
a 2,3-epoxypropyl group;
a group of the formula $-CH_2COOR^1$ in which $R^1$ represents an alkyl group having from 1 to 4 carbon atoms;
a group of the formula

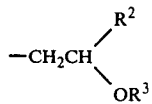

in which
- $R^2$ represents a hydrogen atom, a methyl group or a phenyl group; and
- $R^3$ represents a hydrogen atom or a group of the formula —COR$^{15}$ in which
  - $R^{15}$ is an alkyl group having from 1 to 17 carbon atoms, an alkenyl group having from 2 to 4 carbon atoms, a phenyl group, a benzyl group or a 4-hydroxy-3,5-di-tert-butyl-phenylethyl group; or
- an alkanoyl or alkenoyl group having up to 4 carbon atoms;

when n = 1:

Y represents:
- a hydrogen atom;
- a group of the formula —COR$^{16}$ in which
  - $R^{16}$ represents;
    - an alkyl group having from 1 to 17 carbon atoms,
    - an alkenyl group having from 2 to 5 carbon atoms,
    - an alkynyl group having 2 or 3 carbon atoms, a phenyl group which is unsubstituted or is substituted by a chlorine atom, an alkyl group having from 1 to 4 carbon atoms, an alkoxy group having from 1 to 8 carbon atoms, a hydroxy group or a nitro group, or
    - a 4-hydroxy-3,5-di-tert-butylphenyl group,
    - a benzyl or phenylethyl group,
    - a 4-hydroxy-3,5-di-tert-butyl-phenylethyl group,
    - a naphthyl group,
    - a styryl group,
    - a cyclohexyl group, or
    - a phenoxymethyl group;
- a group of the formula —CO—R$^5$—COO—alkyl in which
  - $R^5$ represents an alkylene group having from 1 to 8 carbon atoms or a phenylene group, and the alkyl has from 1 to 4 carbon atoms;
- a group of the formula —SO$_2$—R$^6$ in which
  - $R^6$ represents a methyl, phenyl or tolyl group;
- a group of the formula

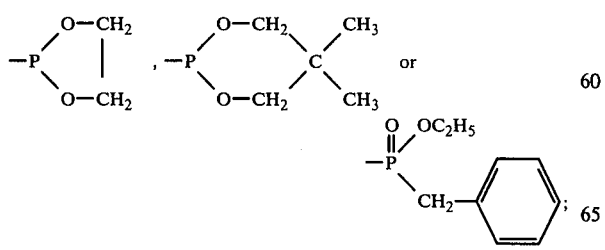

a group of the formula

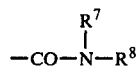

in which
- $R^7$ represents a hydrogen atom, a methyl, phenyl or benzyl group; and
- $R^8$ represents an alkyl group having from 1 to 18 carbon atoms,
  a phenyl group which may be unsubstituted or substituted by a chlorine atom or a methyl group,
  a naphthyl group, a benzyl group, a phenylethyl group or a cyclohexyl group; or
- $R^7$ and $R^8$ together with the nitrogen atom to which they are attached represent a piperidino group, a 1-pyrrolidinyl group or a morpholino group;

an alkyl group having from 1 to 18 carbon atoms;
an allyl group;
a benzyl group;
a cyclohexyl group; or
a group of the formula

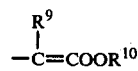

in which
- $R^9$ represents a hydrogen atom or a methyl group; and
- $R^{10}$ represents a methyl or ethyl group;

when n = 2:

Y represents;
- a group of the formula —CO—(R$^{17}$)$_m$—CO— in which
  - m is 0 or 1; and
  - $R^{17}$ represents an alkylene group having from 1 to 10 carbon atoms, a group of the formula —CH$_2$CH$_2$—S—CH$_2$CH$_2$— or —CH=CH—, a phenylene group, a cyclohexylene group or a 2,5-thiophenediyl group;
- a carbonyl group;
- a sulphinyl group;
- a group of the formula >P-phenyl;

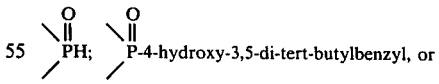

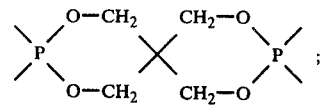

a group of the formula —CO—NH—R$^{12}$—NH—CO— in which
- $R^{12}$ represents an alkylene group having from 2 to 10 carbon atoms, a phenylene group, a tolylene group, a xylylene group, a naphthylene group, a cyclohexylene group or a group of the formula

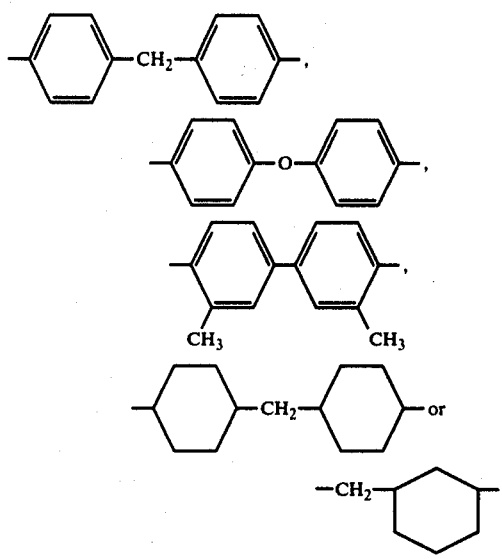

an alkylene group having from 2 to 6 carbon atoms;
a 2-butenylene group;
a m-xylylene group; or
a group of the formula

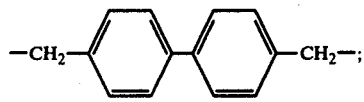

when n = 3:

Y represents a group of formula

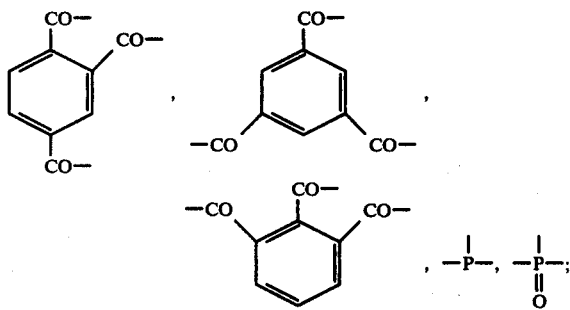

and, when n = 4:

Y represents a group of the formula

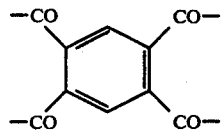

11. A polymer composition according to claim 10, wherein Y is as defined but other than hydrogen.

12. A polymer composition according to claim 1, wherein:

$R^a$, $R^c$ and $R^e$ each represents methyl groups;
$R^b$ represents a hydrogen atom;
$R^d$ and $R^f$ each represents ethyl groups;

X represents a hydrogen atom, a methyl group, an allyl group, a benzyl group, a 2,3-epoxypropyl group, or a group of the formula —$CH_2CH_2OR^3$ in which $R^3$ represents a hydrogen atom, an alkanoyl group having from 2 to 18 carbon atoms or a benzoyl group;

n is 1, 2 or 3;

when n is 1:

Y represents a group of the formula —$COR^{16}$ in which $R^{16}$ represents an alkyl group having from 1 to 17 carbon atoms, a phenyl group which is unsubstituted or has up to three $C_{1-4}$ alkyl and/or hydroxy substituents, or a 4-hydroxy-3,5-di-tert-butyl-phenethyl group; or a group of the formula —CO—$NHR^8$ in which $R^8$ represents an alkyl group having from 1 to 18 carbon atoms, a phenyl group or a cyclohexyl group; and when n = 2:

Y represents a group of the formula —CO—($R^{17}$—)$_m$—CO— in which m is 0 or 1; and $R^{17}$ represents an alkylene group having from 1 to 10 carbon atoms, a group of the formula —$CH_2CH_2SCH_2CH_2$— or a phenylene group;

a sulphinyl group; or a group of the formula —CO—NH—$R^{12}$—NH—CO— in which $R^{12}$ represents a hexamethylene group, a 2,4-tolylene group or a methylenedi-p-phenylene group.

13. A polymer composition according to claim 12, wherein n is 1 and Y represents a group of the formula —$COR^{16}$, or n is 2 and Y represents a group of the formula —CO—$R^{17}$—CO— wherein $R^{16}$ and $R^{17}$ are as defined in claim 12.

14. A polymer composition according to claim 13, wherein X represents a hydrogen atom, a methyl group, an allyl group, a benzyl group or a 2,3-epoxypropyl group.

15. A polymer composition according to claim 14, wherein n = 1 and Y represents a group of the formula —$COR^{16}$ ($R^{16}$ represents an alkyl group having from 1 to 17 carbon atoms or a phenyl group), or n = 2 and Y represents a group of the formula —CO—$R^{17}$—CO— ($R^{17}$ represents an alkylene group having from 1 to 10 carbon atoms).

16. A polymer composition according to claim 1, wherein said 4-piperidinol derivative is selected from the group consisting of:

2,6-diethyl-2,3,6-trimethyl-4-piperidyl stearate,
2,6-diethyl-2,3,6-trimethyl-4-piperidyl crotonate,
2,6-diethyl-2,3,6-trimethyl-4-piperidyl benzoate,
2,6-diethyl-2,3,6-trimethyl-4-piperidyl p-t-butylbenzoate,
2,6-diethyl-2,3,6-trimethyl-4-piperidyl β-(4-hydroxy-3,5-di-t-butylphenyl)-propionate,
1-(2,3-epoxypropyl)-2,6-diethyl-2,3,6-trimethyl-4-piperidyl benzoate,
1-(2-acetoxyethyl)-2,6-diethyl-2,3,6-trimethyl-4-piperidyl benzoate,
1-(2-benzoyloxyethyl)-2,6-diethyl-2,3,6-trimethyl-4-piperidyl benzoate,
1-acetyl-2,6-diethyl-2,3,6-trimethyl-4-piperidyl benzoate,
bis(2,6-diethyl-2,3,6-trimethyl-4-piperidyl)sebacate,
bis(2,6-diethyl-2,3,6-trimethyl-4-piperidyl)terephthalate,
tris(2,6-diethyl-2,3,6-trimethyl-4-piperidyl)phosphite, and acid addition salt thereof.

* * * * *